(12) United States Patent
Weadock et al.

(10) Patent No.: US 8,800,567 B2
(45) Date of Patent: Aug. 12, 2014

(54) IMPLANT SYSTEMS AND METHODS FOR TREATING OBSTRUCTIVE SLEEP APNEA

(75) Inventors: Kevin S. Weadock, Hillsborough, NJ (US); Robert A. Rousseau, Ottsville, PA (US); John R. Jacobs, Easton, PA (US)

(73) Assignee: Ethicon, Inc., Somerville, NJ (US)

( * ) Notice: Subject to any disclaimer, the term of this patent is extended or adjusted under 35 U.S.C. 154(b) by 1054 days.

(21) Appl. No.: 12/578,271

(22) Filed: Oct. 13, 2009

(65) Prior Publication Data

US 2010/0137905 A1 Jun. 3, 2010

Related U.S. Application Data

(63) Continuation-in-part of application No. 12/325,350, filed on Dec. 1, 2008.

(51) Int. Cl.
| | | |
|---|---|---|
| A61F 5/37 | (2006.01) | |
| A61F 5/56 | (2006.01) | |
| A61C 5/14 | (2006.01) | |
| A61B 19/00 | (2006.01) | |
| A61F 2/20 | (2006.01) | |
| A61F 2/02 | (2006.01) | |
| A61F 2/08 | (2006.01) | |
| A61B 17/56 | (2006.01) | |
| A61B 17/70 | (2006.01) | |

(52) U.S. Cl.
USPC ........... 128/848; 128/846; 128/860; 128/897; 128/898; 128/899

(58) Field of Classification Search
USPC ................. 128/846, 848, 860, 897, 898, 899; 623/9, 11.11, 14.13, 17.17; 602/902; 606/53, 60, 251, 263
See application file for complete search history.

(56) References Cited

U.S. PATENT DOCUMENTS

| | | |
|---|---|---|
| 3,123,077 A | 3/1964 | Alcamo |
| 3,378,010 A | 4/1968 | Codling et al. |
| 4,069,825 A | 1/1978 | Akiyama |
| 4,290,763 A | 9/1981 | Hurst |
| 4,557,264 A | 12/1985 | Hinsch |

(Continued)

FOREIGN PATENT DOCUMENTS

| | | |
|---|---|---|
| CN | 2465680 | 9/2011 |
| CN | 102198010 A | 9/2011 |

(Continued)

OTHER PUBLICATIONS

Cole, et al., "Snoring: A Review and a Reassessment", Journal of Otolaryngology, pp. 303-306 (1995).

(Continued)

*Primary Examiner* — Patricia Bianco
*Assistant Examiner* — Nihir Patel

(57) ABSTRACT

A system, method and kit for treating obstructive sleep apnea. The system includes a first implant adapted for implantation in an inframandibular region and having at least one aperture therethrough, and a ribbon-like element having first and second ends and a substantially uniform, non-circular cross section along its length. The ribbon-like element is adapted for implantation in a tongue with the first and second ends extending through the at least one aperture in the first implant for coupling the ribbon-like element with the first implant.

7 Claims, 25 Drawing Sheets

(56) References Cited

U.S. PATENT DOCUMENTS

| | | |
|---|---|---|
| 4,839,215 A | 6/1989 | Starling et al. |
| 4,881,939 A | 11/1989 | Newman |
| 4,950,285 A | 8/1990 | Wilk |
| 5,053,047 A | 10/1991 | Yoon |
| 5,123,913 A | 6/1992 | Wilk et al. |
| 5,269,783 A | 12/1993 | Sander |
| 5,284,161 A | 2/1994 | Karell |
| 5,311,028 A | 5/1994 | Glavish |
| 5,393,984 A | 2/1995 | Glavish |
| 5,483,077 A | 1/1996 | Glavish |
| 5,484,444 A | 1/1996 | Braunschweiler et al. |
| 5,609,559 A | 3/1997 | Weitzner |
| 5,683,417 A | 11/1997 | Cooper |
| 5,704,895 A | 1/1998 | Scott et al. |
| 5,792,067 A | 8/1998 | Karell |
| 5,843,077 A | 12/1998 | Edwards |
| 5,931,855 A | 8/1999 | Buncke |
| 6,161,541 A | 12/2000 | Woodson |
| 6,241,747 B1 | 6/2001 | Ruff |
| 6,250,307 B1 | 6/2001 | Conrad et al. |
| 6,348,156 B1 | 2/2002 | Vishnoi et al. |
| 6,431,174 B1 | 8/2002 | Knudson et al. |
| 6,432,437 B1 | 8/2002 | Hubbard |
| 6,457,472 B1 | 10/2002 | Schwartz et al. |
| 6,513,530 B2 | 2/2003 | Knudson et al. |
| 6,523,542 B2 | 2/2003 | Knudson et al. |
| 6,578,580 B2 | 6/2003 | Conrad et al. |
| 6,589,549 B2 | 7/2003 | Shih et al. |
| 6,599,310 B2 | 7/2003 | Leung et al. |
| 6,627,600 B2 | 9/2003 | Boutignon |
| 6,634,362 B2 | 10/2003 | Conrad et al. |
| 6,638,284 B1 | 10/2003 | Rousseau et al. |
| 6,716,251 B1 | 4/2004 | Asius et al. |
| 6,742,524 B2 | 6/2004 | Knudson et al. |
| 6,755,868 B2 | 6/2004 | Rousseau |
| 6,800,082 B2 | 10/2004 | Rousseau |
| 6,899,105 B2 | 5/2005 | Krueger et al. |
| 6,955,172 B2 | 10/2005 | Nelson et al. |
| 6,981,944 B2 | 1/2006 | Jamiolkowski et al. |
| 7,017,582 B2 | 3/2006 | Metzer et al. |
| 7,056,331 B2 | 6/2006 | Kaplan et al. |
| 7,135,189 B2 | 11/2006 | Knapp |
| 7,146,981 B2 | 12/2006 | Knudson et al. |
| 7,166,570 B2 | 1/2007 | Hunter et al. |
| 7,213,599 B2 | 5/2007 | Conrad et al. |
| 7,237,554 B2 | 7/2007 | Conrad et al. |
| 7,261,702 B1 | 8/2007 | Alexandre et al. |
| 7,288,075 B2 | 10/2007 | Parihar et al. |
| 7,297,102 B2 | 11/2007 | Smith et al. |
| 7,322,993 B2 | 1/2008 | Metzger et al. |
| 7,337,781 B2 | 3/2008 | Vassallo |
| 7,360,432 B2 | 4/2008 | Lehtonen |
| 7,360,542 B2 | 4/2008 | Nelson et al. |
| 7,367,340 B2 | 5/2008 | Nelson et al. |
| 7,401,611 B2 | 7/2008 | Conrad et al. |
| 7,442,389 B2 | 10/2008 | Quelle et al. |
| 7,601,164 B2 | 10/2009 | Wu |
| 7,669,603 B2 | 3/2010 | Knudson et al. |
| 7,806,908 B2 | 10/2010 | Ruff |
| 7,850,894 B2 | 12/2010 | Lindh, Sr. et al. |
| 7,857,829 B2 | 12/2010 | Kaplan et al. |
| 7,888,119 B2 | 2/2011 | Sugaya et al. |
| 8,142,422 B2 | 3/2012 | Makower et al. |
| 2001/0037133 A1 | 11/2001 | Knudson et al. |
| 2003/0004579 A1 | 1/2003 | Rousseau et al. |
| 2003/0034312 A1 | 2/2003 | Unger et al. |
| 2003/0149445 A1 | 8/2003 | Knudson et al. |
| 2003/0149447 A1 | 8/2003 | Morency et al. |
| 2003/0176875 A1 | 9/2003 | Anderson et al. |
| 2004/0020492 A1 | 2/2004 | Dubrul et al. |
| 2004/0020498 A1 | 2/2004 | Knudson et al. |
| 2004/0028676 A1 | 2/2004 | Klein et al. |
| 2004/0102796 A1 | 5/2004 | Hill et al. |
| 2004/0139975 A1 | 7/2004 | Nelson et al. |
| 2004/0144395 A1 | 7/2004 | Evans et al. |
| 2004/0147811 A1 | 7/2004 | Diederich et al. |
| 2004/0149290 A1 | 8/2004 | Nelson et al. |
| 2004/0153127 A1 | 8/2004 | Gordon et al. |
| 2004/0231678 A1 | 11/2004 | Fierro |
| 2005/0038472 A1 | 2/2005 | Furst |
| 2005/0082452 A1 | 4/2005 | Kirby |
| 2005/0092334 A1 | 5/2005 | Conrad et al. |
| 2005/0115572 A1 | 6/2005 | Brooks et al. |
| 2005/0121039 A1 | 6/2005 | Brooks et al. |
| 2005/0159637 A9 | 7/2005 | Nelson et al. |
| 2005/0165352 A1 | 7/2005 | Henry et al. |
| 2005/0199248 A1 | 9/2005 | Pflueger et al. |
| 2005/0203576 A1 | 9/2005 | Sulamanidze et al. |
| 2005/0251255 A1 | 11/2005 | Metzger et al. |
| 2005/0267321 A1 | 12/2005 | Shadduck |
| 2005/0267531 A1 | 12/2005 | Ruff et al. |
| 2005/0267532 A1 | 12/2005 | Wu |
| 2005/0267571 A1 | 12/2005 | Spence et al. |
| 2005/0279365 A1 | 12/2005 | Armijo et al. |
| 2006/0005843 A9 | 1/2006 | Nelson et al. |
| 2006/0079935 A1 | 4/2006 | Kolster |
| 2006/0083767 A1 | 4/2006 | Deusch et al. |
| 2006/0093644 A1 | 5/2006 | Quelle et al. |
| 2006/0150986 A1 | 7/2006 | Roue et al. |
| 2006/0185673 A1 | 8/2006 | Critzer et al. |
| 2006/0206197 A1 | 9/2006 | Morsi |
| 2006/0207608 A1 | 9/2006 | Hirotsuka et al. |
| 2006/0207612 A1 | 9/2006 | Jackson et al. |
| 2006/0228391 A1 | 10/2006 | Seyedin et al. |
| 2006/0241339 A1 | 10/2006 | Cook et al. |
| 2006/0266369 A1 | 11/2006 | Atkinson |
| 2006/0289015 A1 | 12/2006 | Boucher et al. |
| 2007/0000497 A1 | 1/2007 | Boucher et al. |
| 2007/0005109 A1 | 1/2007 | Popadiuk et al. |
| 2007/0005110 A1 | 1/2007 | Collier et al. |
| 2007/0102010 A1 | 5/2007 | Lemperle et al. |
| 2007/0110788 A1 | 5/2007 | Hissong et al. |
| 2007/0119463 A1 | 5/2007 | Nelson et al. |
| 2007/0123996 A1 | 5/2007 | Sugaya et al. |
| 2007/0144531 A1 | 6/2007 | Tomas et al. |
| 2007/0144534 A1 | 6/2007 | Mery et al. |
| 2007/0144535 A1 | 6/2007 | Hegde et al. |
| 2007/0190108 A1 | 8/2007 | Datta et al. |
| 2007/0204866 A1 | 9/2007 | Conrad et al. |
| 2007/0209665 A1 | 9/2007 | Gillis et al. |
| 2007/0227545 A1 | 10/2007 | Conrad et al. |
| 2007/0233276 A1 | 10/2007 | Conrad et al. |
| 2007/0246052 A1 | 10/2007 | Hegde et al. |
| 2007/0256693 A1 | 11/2007 | Paraschac et al. |
| 2007/0257395 A1 | 11/2007 | Lindh et al. |
| 2007/0261701 A1 | 11/2007 | Sanders |
| 2007/0270631 A1 | 11/2007 | Nelson et al. |
| 2007/0272257 A1 | 11/2007 | Nelson et al. |
| 2007/0288057 A1 | 12/2007 | Kuhnel |
| 2007/0295338 A1 | 12/2007 | Loomas et al. |
| 2007/0295340 A1 | 12/2007 | Buscemi |
| 2008/0023012 A1 | 1/2008 | Dineen et al. |
| 2008/0035158 A1 | 2/2008 | Pflueger et al. |
| 2008/0035160 A1 | 2/2008 | Woodson |
| 2008/0066764 A1 | 3/2008 | Paraschac et al. |
| 2008/0066765 A1 | 3/2008 | Paraschac et al. |
| 2008/0066767 A1 | 3/2008 | Paraschac et al. |
| 2008/0066769 A1 | 3/2008 | Dineen et al. |
| 2008/0078411 A1 | 4/2008 | Buscemi et al. |
| 2008/0146868 A1 | 6/2008 | Henri Robert et al. |
| 2008/0167614 A1 | 7/2008 | Tolkowsky et al. |
| 2008/0199824 A1 | 8/2008 | Hargadon |
| 2008/0208265 A1 | 8/2008 | Frazier et al. |
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0165803 A1 | 7/2009 | Bhat et al. |
| 2010/0023055 A1 | 1/2010 | Rousseau |
| 2010/0024830 A1 | 2/2010 | Rousseau et al. |
| 2010/0030011 A1 | 2/2010 | Weadock et al. |
| 2010/0037901 A1 | 2/2010 | Rousseau et al. |
| 2010/0080791 A1 | 4/2010 | Rousseau et al. |
| 2010/0106246 A1 | 4/2010 | Rousseau et al. |
| 2010/0108077 A1* | 5/2010 | Lindh et al. .................. 128/848 |

(56) References Cited

U.S. PATENT DOCUMENTS

| | | | |
|---|---|---|---|
| 2010/0132719 | A1 | 6/2010 | Jacobs et al. |
| 2010/0137794 | A1 | 6/2010 | Knudson et al. |
| 2010/0137905 | A1 | 6/2010 | Weadock et al. |
| 2010/0163056 | A1 | 7/2010 | Tschopp et al. |
| 2010/0211184 | A1 | 8/2010 | Rousseau et al. |
| 2010/0234794 | A1 | 9/2010 | Weadock et al. |
| 2010/0234946 | A1 | 9/2010 | Rousseau |
| 2010/0294284 | A1 | 11/2010 | Hohenhorst et al. |
| 2010/0319710 | A1 | 12/2010 | Sharkawy et al. |
| 2011/0100376 | A1 | 5/2011 | Rousseau |
| 2011/0100377 | A1 | 5/2011 | Weadock et al. |
| 2011/0100378 | A1 | 5/2011 | Rousseau |
| 2011/0144558 | A1 | 6/2011 | Rousseau |
| 2011/0174315 | A1 | 7/2011 | Zhang et al. |
| 2011/0178439 | A1 | 7/2011 | Irwin et al. |
| 2012/0245629 | A1 | 9/2012 | Gross et al. |
| 2013/0074849 | A1 | 3/2013 | Rousseau et al. |
| 2013/0098371 | A1 | 4/2013 | Rousseau et al. |
| 2013/0118505 | A1 | 5/2013 | Rousseau et al. |
| 2013/0150872 | A1 | 6/2013 | Rousseau |
| 2013/0174857 | A1 | 7/2013 | Rousseau et al. |
| 2013/0186412 | A1 | 7/2013 | Weadock et al. |

FOREIGN PATENT DOCUMENTS

| | | |
|---|---|---|
| DE | 10245076 A1 | 4/2004 |
| EP | 2145587 A2 | 1/2010 |
| EP | 2517633 A1 | 10/2012 |
| FR | 2651113 A1 | 3/1991 |
| JP | 2003265621 | 9/2003 |
| SU | 927236 B | 5/1982 |
| WO | WO 99/00058 A1 | 1/1999 |
| WO | WO 00/66050 | 11/2000 |
| WO | WO 01/21107 A1 | 3/2001 |
| WO | WO 03/096928 A1 | 11/2003 |
| WO | WO 2004/020492 | 3/2004 |
| WO | WO 2004/021869 A2 | 3/2004 |
| WO | WO 2004/021870 A2 | 3/2004 |
| WO | WO 2004/021870 A3 | 3/2004 |
| WO | WO 2004/060311 A2 | 7/2004 |
| WO | WO 2004/060311 A3 | 7/2004 |
| WO | WO 2004/084709 A2 | 10/2004 |
| WO | WO 2004/084709 A3 | 10/2004 |
| WO | WO 2005/046554 A2 | 5/2005 |
| WO | WO 2005/046554 A3 | 5/2005 |
| WO | WO 2005/051292 A2 | 6/2005 |
| WO | WO 2005/082452 | 9/2005 |
| WO | WO 2005/122954 A1 | 12/2005 |
| WO | WO 2006/012188 A1 | 2/2006 |
| WO | WO 2006/072571 A1 | 7/2006 |
| WO | WO 2006/108145 A1 | 10/2006 |
| WO | WO 2007/056583 A1 | 5/2007 |
| WO | WO 2007/075394 A2 | 7/2007 |
| WO | WO 2007/075394 A3 | 7/2007 |
| WO | WO 2007/132449 | 11/2007 |
| WO | WO 2007/134005 A1 | 11/2007 |
| WO | WO 2007/146338 A2 | 12/2007 |
| WO | WO 2007/149469 A2 | 12/2007 |
| WO | WO 2007/149469 A3 | 12/2007 |
| WO | WO 2008/118913 A2 | 10/2008 |
| WO | WO 2009/023256 A2 | 2/2009 |
| WO | WO 2009/036094 | 3/2009 |
| WO | WO 2010/019376 A2 | 2/2010 |
| WO | WO 2010/035303 A1 | 4/2010 |
| WO | WO 2010/065341 A2 | 6/2010 |
| WO | WO 2010/065341 A3 | 6/2010 |
| WO | WO 2012/041205 A1 | 4/2012 |
| WO | WO 2012/064902 A2 | 5/2012 |
| WO | WO 2012/170468 | 12/2012 |

OTHER PUBLICATIONS

Harries, et al., "The Surgical Treatment of Snoring", Journal of Laryngology and Otology, pp. 1105-1106(1996).

Huang, et al., "Biomechanics of Snoring", Endeavour, vol. 19(3): p. 96-100 (1995).

Pang, et al., "Tongue Suspension Suture in Obstructive Sleep Apnea", Operative Techniques in Otolaryngology, V. 17, No. 4, pp. 252-256 (2006).

Repose Genioglossus Advancement, Influent Medical, www.influent.com, 1 page.

Schwab, et al., "Upper airway and soft tissue changes induced by CPAP in normal subjects", Am. J. Respit. Crit. Care Med., vol. 154, No. 4, pp. 1106-1116 (1996).

Schwartz, et al., "Effects of electrical stimulation to the soft palate on snoring and obstructive sleep apnea", J. Prosthetic Dentistry, pp. 273-281 (1986).

Schamsuzzaman, et al., "Obstructive Sleep Apnea: Implications for Cardiac and Vascular Disease", JAMA vol. 290: (14); pp. 1906-1914.

The Advance System, Aspire Medical, Inc., www.aspiremedical.com, 3 pp.

The Pillar Procedure, Restore Medical, Inc., www.restoremedical.com 2 pp.

Wiltfang, et al., "First results on daytime submandibular elxtrostimulation of suprahyoidal muscles to prevent night-time hypopharynegeal collapse in obstructive sleep apnea syndrome", International Journal of Oral & Maxillofacial Surgery, pp. 21-25 (1999).

U.S. Appl. No. 12/182,402, filed Jul. 30, 2008.
U.S. Appl. No. 12/183,955, filed Jul. 31, 2008.
U.S. Appl. No. 12/228,681, filed Aug. 14, 2008.
U.S. Appl. No. 12/238,991, filed Sep. 26, 2008.
U.S. Appl. No. 12/257,563, filed Oct. 24, 2008.
U.S. Appl. No. 12/261,102, filed Oct. 30, 2008.
U.S. Appl. No. 12/378,573, filed Feb. 17, 2009.
U.S. Appl. No. 12/402,631, filed Mar. 12, 2009.

Schleef et al., "Cytokine Activation of Vascular Endothelium, Effects on Tissue-Type 1 Plasminogen Activator Inhibitor" The J. of Biological Chem., vol. 263, No. 12, pp. 5797-5803 (1988).

Teles et al., "Use of Palatal Lift Prosthesis on Patient Submitted to Maxillectomy: A Case Report", Applied Cancer Res. vol. 25(3), pp. 151-154 (2005).

Vicente et al., "Tongue-Base Suspension in Conjunction with Uvulopapatopharyngoplasty for Treatment of Severe Obstructive Sleep Apnea: Long-term Follow-Up Results", The Laryngoscope, vol. 116 pp. 1223-1227 (2006).

Wassmuth et al., "Cautery-assisted palatal stiffening operation for the treatment of obstructive sleep apnea syndrome", Otolaryngology—Head and Neck Surgery, vol. 123, pp. 55-60 (2000).

U.S. Appl. No. 13/486,293, filed Jun. 1, 2012.

Notification of Transmittal of the International Search Report and the Written Opinion of the International Search Authority or the Declaration mailed on Feb. 3, 2010; PCT/US2009/051921; International Filing Date: Jul. 28, 2009.

Notification of Transmittal of the International Search Report and the Written Opinion of the International Search Authority or the Declaration mailed on May 25, 2010; PCT/US2010/023152; International Filing Date: Apr. 2, 2010.

International Search Report dated Nov. 4, 2009 for International Patent Application No. PCT/US2009/052126.

International Search Report dated Dec. 21, 2009 for International Patent Application No. PCT/US2009/057661.

International Search Report dated Dec. 22, 2009 for International Patent Application No. PCT/US2009/061223.

International Search Report dated Dec. 29, 2009 for International Patent Application No. PCT/US2009/061455.

International Search Report dated Jan. 21, 2010 for International Patent Application No. PCT/US2009/052110.

International Search Report dated May 25, 2010 for International Patent Application No. PCT/US2010/023152.

International Search Report dated May 25, 2010 for International Patent Application No. PCT/US2010/025778.

International Search Report dated Jan. 14, 2011 for International Patent Application No. PCT/US2010/052628.

International Search Report dated Jan. 20, 2011 for International Patent Application No. PCT/US2010/052644.

(56) References Cited

OTHER PUBLICATIONS

International Search Report dated Jan. 24, 2011 for International Patent Application No. PCT/US2010/052649.
International Search Report dated Feb. 28, 2011 for International Patent Application No. PCT/US2010/059673.
International Search Report dated Apr. 9, 2013 for International Patent Application No. PCT/US2012/061569.
International Search Report dated Apr. 2, 2013 for International Patent Application No. PCT/US2012/067708.
Written Opinion dated Nov. 27, 2012 for International Patent Application No. PCT/US2012/056577.

* cited by examiner

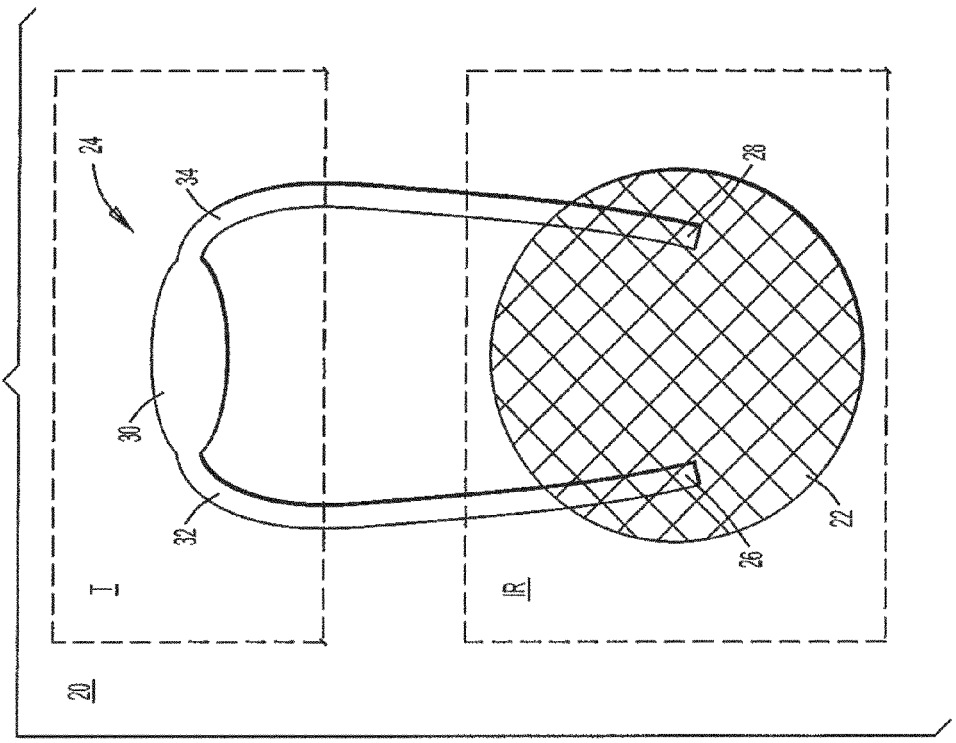
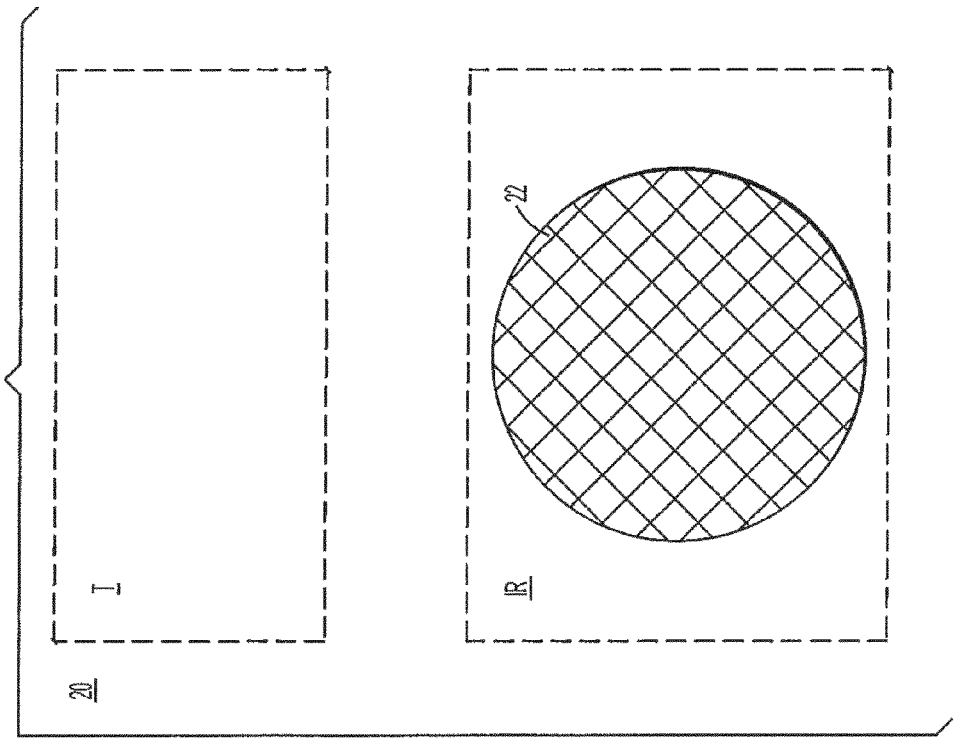

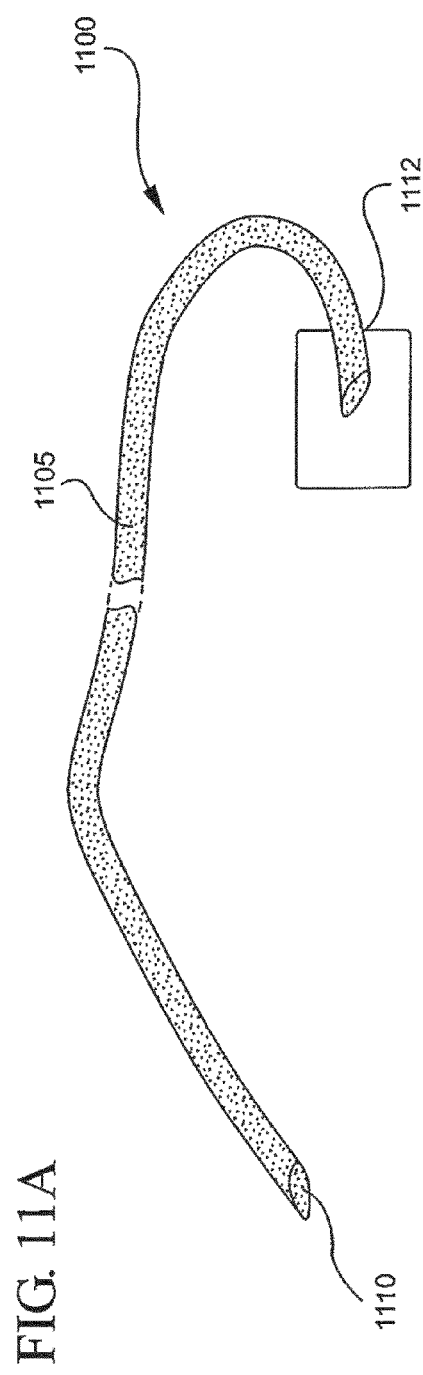
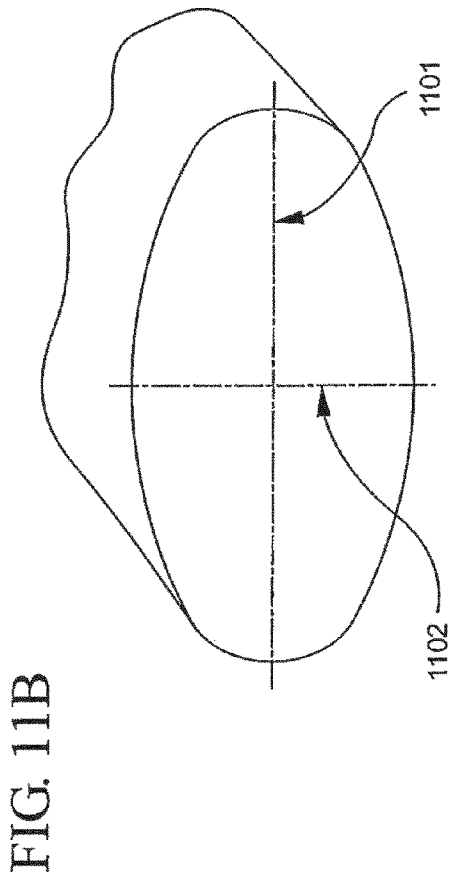
FIG. 11A
FIG. 11B

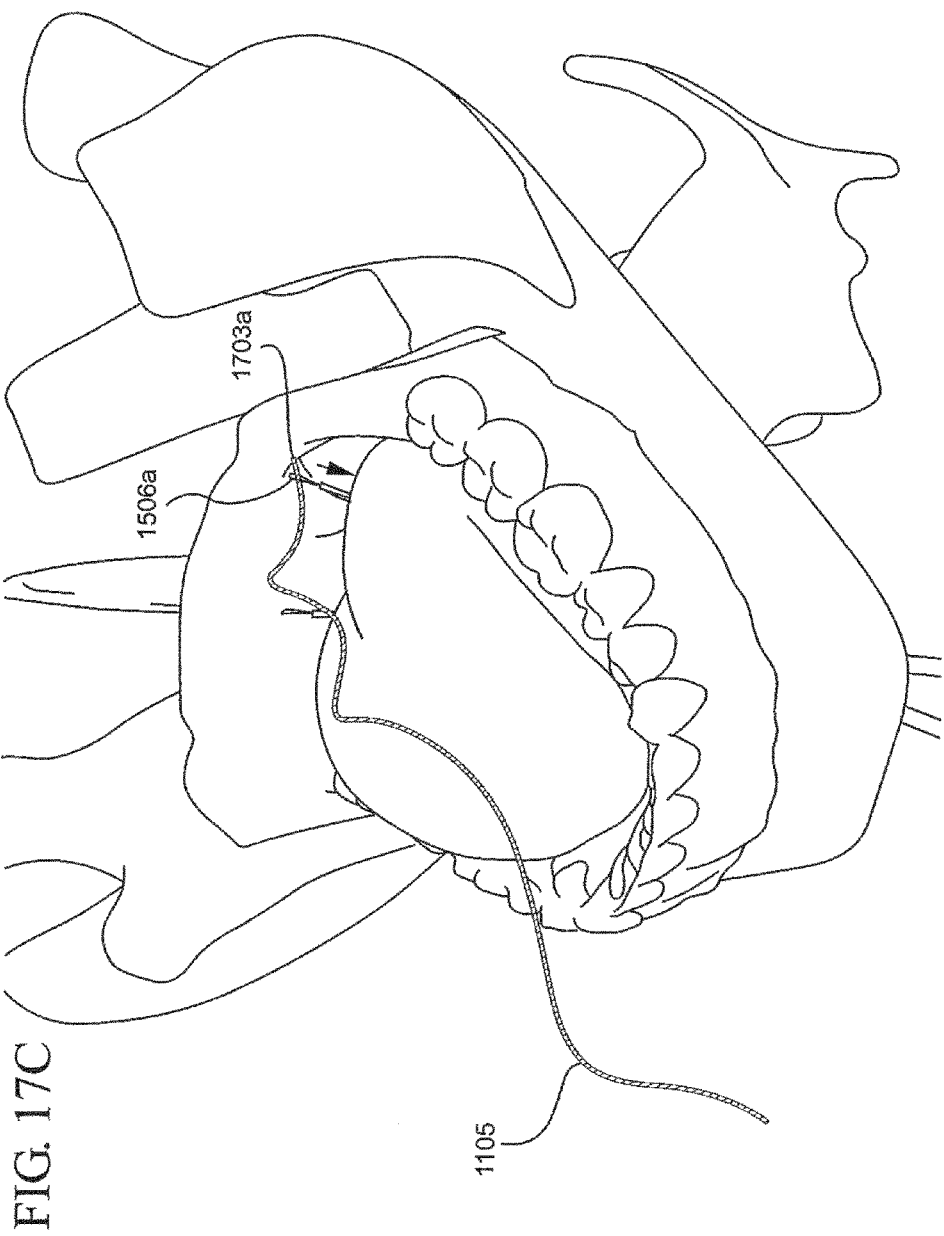

IMPLANT SYSTEMS AND METHODS FOR TREATING OBSTRUCTIVE SLEEP APNEA

CROSS REFERENCE TO RELATED APPLICATIONS

The present application is a continuation-in-part of, and claims priority to, U.S. patent application Ser. No. 12/325,350, filed on Dec. 1, 2008.

FIELD OF THE INVENTION

The present invention generally relates to treating sleep disorders, and more specifically relates to implant systems, devices and methods for treating patients suffering from obstructive sleep apnea.

DESCRIPTION OF THE RELATED ART

Obstructive sleep apnea (OSA) is caused by a blockage of the airway, which usually occurs when the soft tissue in the throat collapses and closes during sleep. According to the National Institutes of Health, OSA affects more than twelve million Americans. During each apnea event, the brain briefly arouses the sufferer in order to initiate the resumption of breathing. This type of sleep, however, is extremely fragmented and of poor quality. When left untreated, OSA may result in high blood pressure, cardiovascular disease, weight gain, impotency, headaches, memory problems, job impairment, and/or motor vehicle crashes. Despite the seriousness of OSA, a general lack of awareness among the public and healthcare professionals results in the vast majority of OSA sufferers remaining undiagnosed and untreated.

There have been a number of efforts directed to treating OSA. For example, devices for electrically stimulating the soft palate to treat snoring and obstructive sleep apnea are disclosed in U.S. Pat. Nos. 5,284,161 and 5,792,067. These devices have had mixed results because they require patient adherence to a regimen of use, subject the patient to discomfort during sleep, and result in repeated arousal of the patient.

Another treatment, commonly referred to as continuous positive airway pressure (CPAP), delivers air into a patient's airway through a specially designed nasal mask or pillow. The flow of air creates positive pressure when the patient inhales to keep the airway open. CPAP is considered by many to be an effective non-surgical treatment for the alleviation of snoring and obstructive sleep apnea, however, patients complain about discomfort caused by the mask and hoses, including bloating, nasal drying, and dry eyes. As a result, patient compliance for CPAP is only about 40%.

Surgical treatments have also been used to treat OSA. One such treatment is referred to as uvulopalatopharyngoplasty, which involves removing about 2 cm of the trailing edge of the soft palate to reduce the soft palate's ability to flutter between the tongue and the pharyngeal wall. Another procedure uses a surgical laser to create scar tissue on the surface of the soft palate, which reduces the flexibility of the soft palate for reducing snoring and/or closing of the air passage. Yet another procedure, commonly referred to as cautery-assisted palatal stiffening operation (CAPSO), is an office-based procedure performed under local anesthesia whereby a midline strip of soft palate mucosa is removed, and the wound is allowed to heal whereupon the flaccid palate is stiffened.

Surgical procedures such as those mentioned above continue to have problems. More specifically, the area of tissue that is surgically treated (i.e., removal of palatal tissue or scarring of palatal tissue) is often larger than is necessary to treat the patient's condition. In addition, the above-mentioned surgical procedures are often painful with extended, uncomfortable healing periods. For example, scar tissue on the soft palate may present a continuing irritant to the patient. Furthermore, the above procedures are not reversible in the event of adverse side effects.

Another implant system, sold under the trademark REPOSE™ by InfluENT of Concord, N.H., uses a titanium bone screw that is inserted into the posterior aspect of the mandible at the floor of the mouth. A loop of suture is passed through the tongue base and attached to the mandibular bone screw. The Repose™ procedure achieves a suspension or hammock of the tongue base making it less likely for the base of the tongue to prolapse during sleep. Due to the high activity of the tongue during wakefulness, however, the suture component of this device may act as a "cheese cutter" to the tongue, causing device failure and requiring subsequent removal.

Another effort for treating OSA involves creating an auxiliary airway for bypassing the clogged portion of the main airway. In one embodiment of commonly assigned U.S. patent application Ser. No. 12/182,402, filed Jul. 30, 2008, the disclosure of which is hereby incorporated by reference herein, an auxiliary airway is formed by implanting an elongated conduit beneath a pharyngeal wall of the pharynx. The elongated conduit has a proximal end in communication with a first region of the pharynx, a distal end in communication with a second region of the pharynx, and an intermediate section extending beneath the pharyngeal wall for bypassing an oropharynx region of the pharynx.

Magnets have also been used for treating OSA. For example, in one embodiment of commonly assigned U.S. patent application Ser. No. 12/183,955, filed Jul. 31, 2008, the disclosure of which is hereby incorporated by reference herein, a magnetic implant includes a bone anchor, a first magnet coupled to the bone anchor, a tongue anchor, a second magnet coupled to the tongue anchor, and a support for aligning the first and second magnets so that a repelling force is generated between the magnets for urging the second magnet away from the first magnet and toward the bone anchor. The support maintains the first magnet at a fixed distance from the bone anchor, aligns the first magnet with the second magnet, and guides movement of the first and second magnets. The magnetic implant disclosed in one or more embodiments of the '955 application does not have a hard stop so as to avoid the "cheese-cutter" effect observed when using implants having a hard stop.

In one embodiment of commonly assigned U.S. patent application Ser. No. 12/261,102, filed Oct. 30, 2008, the disclosure of which is hereby incorporated by reference herein, an implant for treating obstructive sleep apnea includes an elongated element having a central area implantable in a tongue, the elongated element including a first arm extending from a first end of the central area and a second arm extending from a second end of the central area, with the first and second arms extending through the tongue and being anchored to the inframandibular musculature.

In spite of the above advances, there remains a need for additional systems, devices and methods for treating OSA through minimally invasive approaches that provide long term results, that encourage patient compliance, and that minimize patient discomfort.

SUMMARY OF THE INVENTION

A system is provided for treating obstructive sleep apnea. The system includes a first implant adapted for implantation in an inframandibular region and having at least one aperture therethrough, and a ribbon-like element having first and second ends and a substantially uniform, non-circular cross section along its length. The ribbon-like element is adapted for implantation in a tongue with the first and second ends extending through the at least one aperture in the first implant for coupling the ribbon-like element with said first implant. The first implant may further include a cover portion, a base portion, and an anchor element positioned therebetween, with the anchor element having at least one aperture therethrough. In alternate embodiments, the anchor element has a stiffness greater than, and is smaller than, said cover and base portions, and/or may be made of a biocompatible, non-resorbable material such as silicon, polyurethane, polypropylene, polyethylene, polyurethane, stainless steel, nitinol, tantalum or titanium. The cover and base portions may also be made a biocompatible mesh or a biocompatible fabric, such as a resorbable mesh or fabric, and the anchor element may also be made of a mesh.

Also provided is a method for treating obstructive sleep apnea including the steps of implanting a first implant having at least one aperture therethrough in an inframandibular region, implanting at least a portion of a ribbon-like element having first and second ends and a substantially uniform, non-circular cross-section along its length in a tongue, passing the first end of the ribbon-like element through the at least one aperture in the first implant, and passing the second end of the ribbon-like implant through the at least one aperture in the first implant.

The method may further include, following the second passing step, coupling the first and second ends of the ribbon-like element together to thereby secure the ribbon-like element to the first implant. Further, prior to the coupling step, the method may further include pulling on the first and/or second ends of the ribbon-like element to thereby adjust the position of the ribbon-like element relative to the first implant, and/or pulling on the first and/or second ends of the ribbon-like element to increase the distance between the base of tongue and the posterior pharyngeal wall. The first implant may be made of a non-resorbable, biocompatible mesh or fabric, and/or include a mesh portion and an anchor having a stiffness greater than the mesh portion and having at least one aperture therethrough.

Finally, a kit is provided for treating sleep apnea that includes a first implant adapted for implantation in an inframandibular region, a ribbon-like element having first and second ends and a substantially uniform, non-circular cross-section along its length, and adapted for implantation in a tongue and for coupling with the first implant, at least one introducer, and at least one snare adapted to be passed through the introducer and having a distal end adapted to couple with the first end of the ribbon-like element.

The kit may further include a suture having first and second ends, and a needle element coupled to the first end. In yet another embodiment, the kit may further include a second ribbon-like element having first and second ends and adapted for implantation in a tongue and for coupling with the first implant. In alternate embodiments, the first ribbon-like element may be made of expanded polytetrafluoroethylene and/or the first implant may further include a cover portion, a base portion, and an anchor element positioned therebetween, with the anchor element having at least one aperture therethrough.

In yet another embodiment, the anchor element is made of a biocompatible, non-resorbable material, such as silicon, polyurethane, polypropylene, polyethylene, polyurethane, stainless steel, nitinol, tantalum or titanium.

In yet another alternative embodiment, the kit further includes a washer that is adapted to be placed between the ribbon-like element and first implant.

In yet another embodiment, the kit further includes a balloon that is adapted to be placed between the ribbon-like element and the first implant. A filling reservoir may be coupled to the balloon.

These and other preferred embodiments of the present invention will be described in more detail below.

BRIEF DESCRIPTION OF THE DRAWINGS

FIG. 4A shows a system for treating obstructive sleep apnea including a first implant part implantable in inframandibular tissue, in accordance with one embodiment of the present invention.

FIG. 4B shows a system for treating obstructive sleep apnea including the first implant part implantable in inframandibular tissue and a second implant part implantable in a tongue, in accordance with one embodiment of the present invention.

FIGS. 11A-11B illustrate one embodiment of a ribbon-like element of an alternative implant system according to the present invention.

FIG. 17a-f illustrate a method for implanting the implant of FIGS. 11-12.

DETAILED DESCRIPTION

Figure 1:
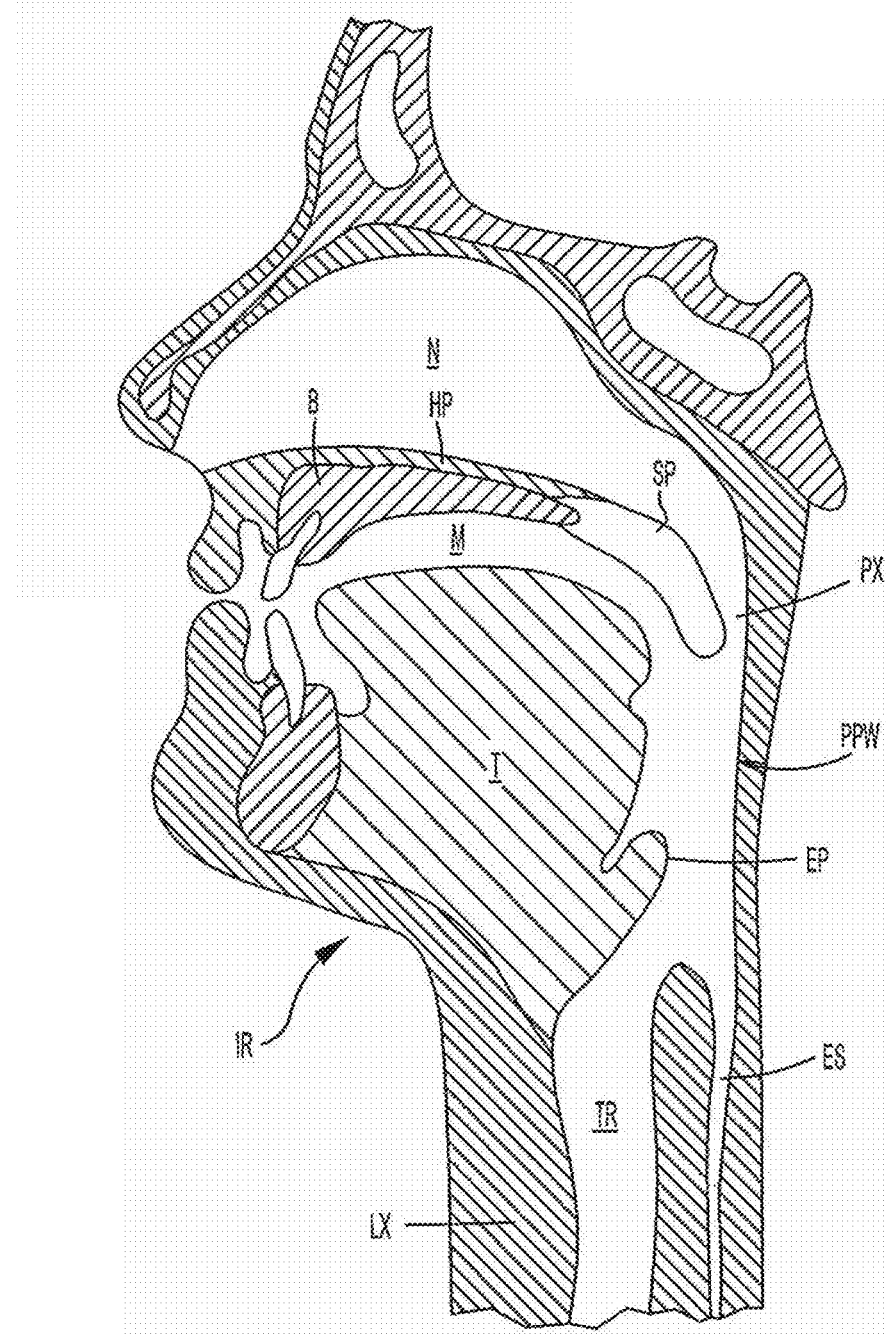
FIG. 1 shows a cross-sectional view of a human head including a nasal cavity and a pharynx.

FIG. 1 shows a cross-section of a human head with anatomical structures including the nasal cavity N, bone B of the hard palate HP, the soft palate SP, the mouth M, the tongue T, the trachea TR, the epiglottis EP, the esophagus ES, and the posterior pharyngeal wall PPW. In the human head, an air filled space between the nasal cavity N and the larynx LX is referred to as the upper airway. The most critical part of the upper airway associated with sleep disorders is the pharynx PX.

Figure 2:
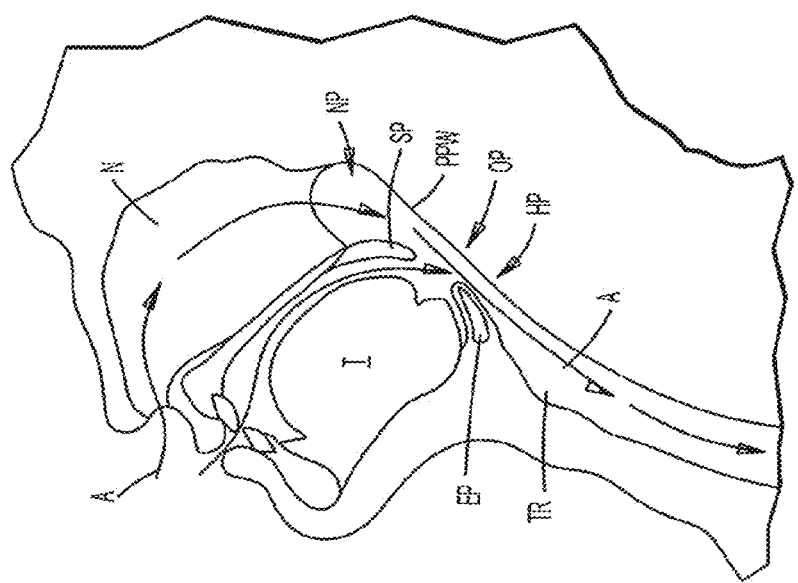
FIG. 2 shows a cross-sectional view of the nasal cavity and the pharynx of a human during normal breathing.

Referring to FIG. 2, the pharynx has three different anatomical levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The hypopharynx HP is the lower portion of the pharynx located below the soft tissue of the oropharynx OP. The oropharynx OP is the section of the pharynx that is most likely to collapse due to the high prevalence of soft tissue structure, which leaves less space for airflow. The hypopharynx HP lies below the aperture of the larynx and behind the larynx, and extends to the esophagus.

As is well known to those skilled in the art, the soft palate and the tongue are both flexible structures. The soft palate SP provides a barrier between the nasal cavity N and the mouth M. In many instances, the soft palate SP is longer than necessary and extends a significant distance between the back of the tongue T and the posterior pharyngeal wall PPW.

Although the muscles relax throughout the body during sleep, most of the muscles of the respiratory system remain active. During inhalation, the diaphragm contracts and causes negative pressure to draw air A into the nasal cavity N and the mouth M. The air then flows past the pharynx PX, through the trachea TR and into the lungs. The negative pressure causes the tissue of the upper airway to deform slightly, which narrows the airway passage. In apneic patients, the soft palate SP, the tongue T, and/or the epiglottis EP collapse against the posterior pharyngeal wall PPW to block airflow into the trachea. As the airway narrows, airflow through the pharynx becomes turbulent which causes the soft palate SP to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep.

If apnea or hypopnea occurs more than five times per hour, most medical personnel diagnose the individual as having an upper airway resistance problem. Many of these patients often exhibit symptoms related to sleep disorders including sleepiness during the day, depression, and difficulty concentrating.

Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

Referring to FIG. 2, when an individual is awake, the back of the tongue T and the soft palate SP maintain their shape and tone due to their respective internal muscles. As a result, the airway A through the pharynx remains open and unobstructed. During sleep, however, the muscle tone decreases and the posterior surface of the tongue and the soft palate become more flexible and distensible.

Figure 3:
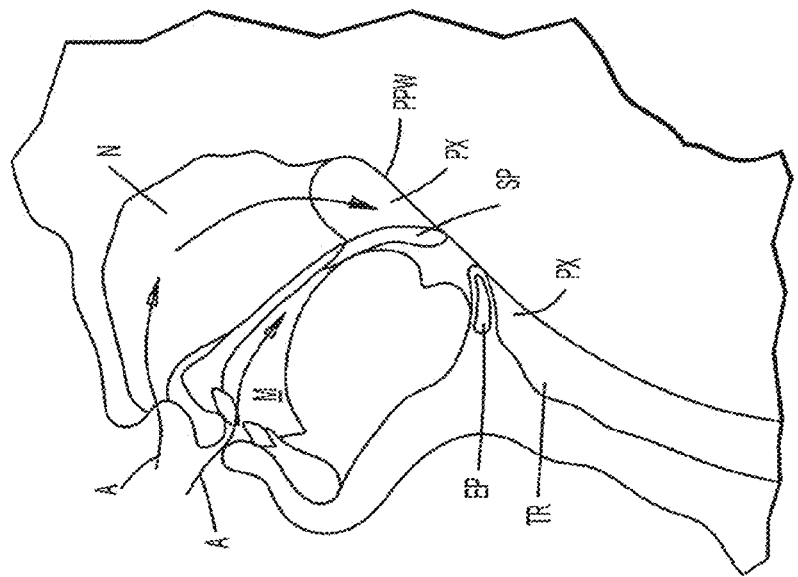
FIG. 3 shows a cross-sectional view of the nasal cavity and the pharynx of a human having an airway that is at least partially closed.

Referring to FIG. 3, without normal muscle tone to keep their shape and to keep them in place either alone or as a group, the posterior surface of the tongue T, the epiglottis EP, and the soft palate SP tend to easily collapse to block the airway A.

Referring to FIG. 4A, in one embodiment an implant 20 used for treating obstructive sleep apnea may include a first implant part 22 or anchoring element implantable in an inframandibular region IR of a head. The first implant part 22 may be implanted between tissue planes in the inframandibular region IR, or alternatively between geniohyoid musculature and mylohyoid musculature, or between mylohyoid and digastrics muscles. The first implant part 22 desirably includes a biocompatible, flexible pad such as a mesh or fabric pad, a woven or knitted mesh, a non-woven or non-knitted mesh, a flat braid comprised of polypropylene or any combination of the above materials. The first implant part 22 may also be made of stainless steel, nitinol, silicone, polyethylene, or polytetrafluoroethylene, and/or resorbable synthetic polymers such as polylactide, polyglycolide, polydioxanone, polycaprolactone, or co-polymers thereof. The first implant part may include a film having openings, pores, or perforations for enabling tissue ingrowth, or may include a resorbable film having non-resorbable particles or fibers that precipitate the formation of scar tissue. A sclerosing agent may be used in combination with the first implant part to encourage the formation of scar tissue on, in and/or around the first implant part. Energy such as laser energy or heat may also be used to form the scar tissue in the inframandibular region. The scar tissue desirably provides a soft tissue anchor in the inframandibular region of an oral cavity, and is preferably a scar plane or scar plate that lies in the inframandibular region. The anchoring element provided in the inframandibular region may also only include scar tissue that is formed without requiring the implantation of a first implant part.

The first implant part or anchoring element 22 may also include a mesh or fabric pad having a sclerosing agent provided thereon that is implanted in the inframandibular region. The mesh or fabric pad is left in place as scar tissue forms at least partially on, in and/or around the mesh or fabric pad. After a period of time, the newly formed scar tissue defines a mass of scar tissue such as a scar plane or scar plate that is disposed in the inframandibular region. The scar tissue preferably provides a soft anchor in the inframandibular region that may be coupled with an implant part disposed in a tongue, or coupled with a hyoid bone.

The first implant part 22 may have a size and shape that may be modified by a surgeon at the time of implantation. In one embodiment, a square of biocompatible mesh or fabric has dimensions of about four inches in length and about four inches in width. During surgery, the surgeon may cut the mesh or fabric into a size and shape reflecting the surgical needs of a patient, such as a rectangle, square, elliptical, or surgical shape.

Referring to FIG. 4B, the implant 20 may further include a second implant part 24 implantable in a tongue T. The second implant part 24 may be elongated and may include a filament, a braided tube, or a braided barbed tube having a first end 26 and a second end 28. The second implant part 24 preferably includes a buttress section 30 at a center portion thereof. The second implant part 24 also desirably includes a first arm 32 extending between the buttress section 30 and the first end 26, and a second arm 34 extending between the buttress section 30 and the second end 28. The buttress section 30 desirably forms the widest and/or largest diameter portion of the second implant part 24, and desirably has a greater width and/or diameter than the diameter of the respective first and second arms 32, 34. The wider buttress section 30 preferably provides enhanced anchoring of the second implant part 24 in the tissue of the tongue T, and minimizes the likelihood of movement of the second implant part in the tongue.

The first and second arms 32, 34 projecting from the buttress may further have barbs. The barbs desirably enhance attachment of the first and second arms of the second implant part to the first implant part and/or the scar plane formed about the first implant part. In one embodiment, the barbs on the respective first and second arms project in opposite directions.

The second implant part 24 may be formed from non-absorbable materials, absorbable materials, or a combination of non-absorbable and absorbable materials. The non-absorbable materials may include polymeric materials such as non-resorbable polymers, silicone, polyethylene terephalate, polytetrafluoroethylene, polyurethane and polypropylene, nitninol, stainless steel, and/or composite materials. Suitable resorbable polymers may include polylactide, polyglycolide copolymers, polycaprolactone, and/or collagen.

The first implant part 22 preferably serves as a "soft anchor" for the second implant part positioned in the tongue. In one embodiment, the spacing between the first implant part 22 and the second implant part 24 may be adjusted by pulling the first and second arms 32, 34 of the second implant part toward the first implant part so as to shorten the length of the arms between the two implant parts. The second implant part in the tongue is preferably advanced in an anterior and/or inferior direction so as to prevent the tongue from sealing against the back wall of the pharynx. The arms are preferably secured to the first implant part so as to maintain the tongue in the forward shifted position. The distal ends 26, 28 of the first and second arms 32, 34 are preferably secured to the first implant part 22 using methods and devices that are described in more detail herein.

Figure 5A:
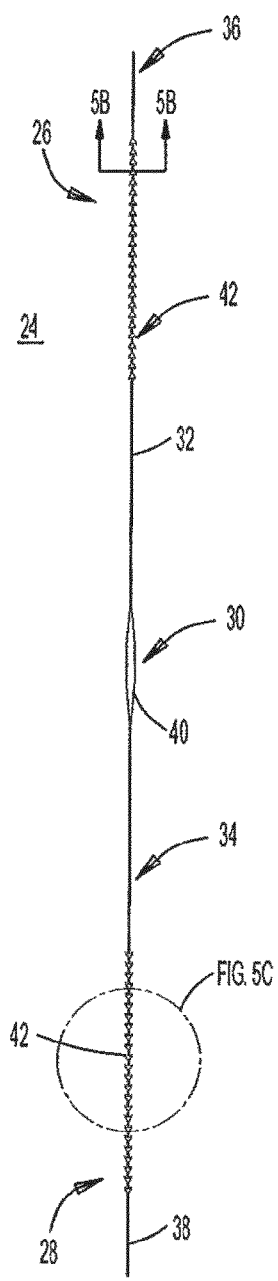
FIGS. 5A-5C show the second implant part of FIG. 4B, in accordance with one embodiment of the present invention.

Referring to FIG. 5A, in one embodiment, the second implant part 24 or tongue implant desirably includes the first end 26 and the second end 28. The elongated second implant part 24 preferably includes the buttress section 30 at the center portion thereof, the first arm 32 located between the buttress section 30 and the first end 26, and a first needle 36 secured to the free end 26 of the first arm 32. The second implant part 24 also preferably includes the second arm 34 extending between the buttress section 30 and the second end 28 thereof, and a second needle 38 secured to the free end 28 of the second arm 34. In one embodiment, the buttress section 30 desirably forms the widest and/or largest diameter portion of the second implant part 24 so that the buttress section 30 has a width or diameter that is greater than the width or diameter of the respective first and second arms 32, 34.

Figure 5B:
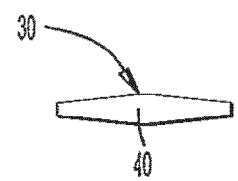

Referring to FIGS. 5A and 5B, the buttress section 30 of the second implant part 24 desirably includes a biocompatible element 40 disposed therein. In one embodiment, the biocompatible element 40 may be placed within a previously implanted second implant part or may be inserted into the center of the second part before implanting the second implant part in tissue. The biocompatible element 40 may have an elliptical shape and may also comprise a biocompatible metal or alloy.

Figure 5C:
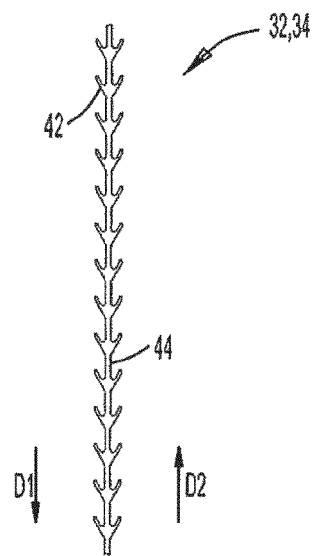

Referring to FIG. 5C, one or more of the first and second arms 32, 34 may include a plurality of barbs 42 that project from a flexible core 44. The plurality of barbs 42 are desirably spaced from one another along the length of the flexible core 44. In one embodiment, the tips of sequentially positioned barbs 42 are about 0.060 inches from one another, and are adapted to collapse inwardly when pulled through tissue in a first direction designated $D_1$, and to engage the tissue for holding the first and second arms 32, 34 in place when pulled in a second direction designated $D_2$. The base portions of the barbs 42 may be staggered along the axis of each arm 32, 34 to either partially oppose each other or to prevent direct opposition of any two barbs along the axis of each arm 32, 34.

Figure 6A:
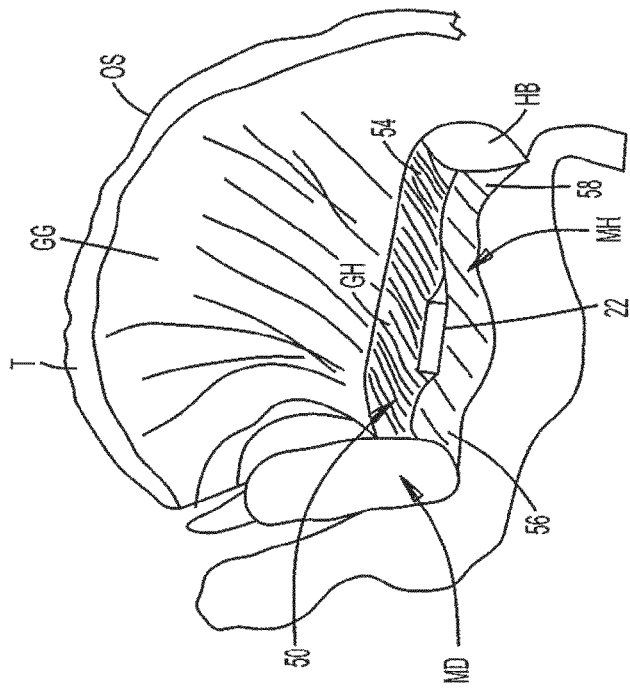
FIGS. 6A and 6B show a method of treating obstructive sleep apnea including implanting a first implant part in an inframandibular region, in accordance with one embodiment of the present invention.
Figure 6B:
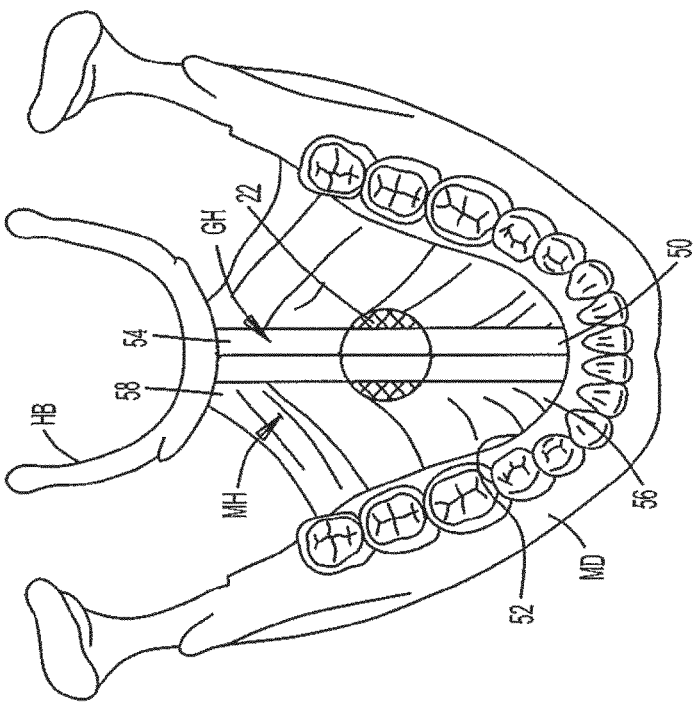

Referring to FIGS. 6A and 6B, an oral cavity of a patient includes a mandible MD, a hyoid bone HB, geniohyoid musculature GH, and mylohyoid musculature MH. The geniohyoid musculature GH has an anterior end 50 connected to an inner surface 52 of the mandible MD, and a posterior end 54 connected to the hyoid bone HB. The mylohyoid musculature MH has an anterior end 56 that is coupled with the inner surface 52 of the mandible MD and a posterior end 58 connected with the hyoid bone HB. The oral cavity also includes the tongue T (FIG. 6B) having genioglossus musculature GG and an outer surface OS.

The first implant part 22 or anchoring element shown and described above may be implanted in inframandibular tissue and more preferably between the geniohyoid musculature GH and the mylohyoid musculature MH. In one embodiment, the first implant part 22 is a porous layer that allows for tissue ingrowth (e.g. scar tissue) into the layers, and is preferably implanted between the geniohyoid musculature GH and the mylohyoid musculature MH as part of a first phase of a surgical procedure. The geniohyoid and mylohyoid muscles are desirably exposed by making a small incision in the tissue fold under the mandible MD. After the first implant part 22 is implanted, the first implant part 22 is left in place so that scar tissue may form in and/or around the first implant part. The scar tissue that forms in and/or around the first implant part preferably forms a scar plane or scar plate extending between the geniohyoid musculature GH and the mylohyoid musculature MH. The scar plane or scar plate desirably forms a soft anchor for a second implant part positioned in a tongue, as will be described in more detail below. The first implant part may be resorbed as the scar tissue forms.

Figure 7B:
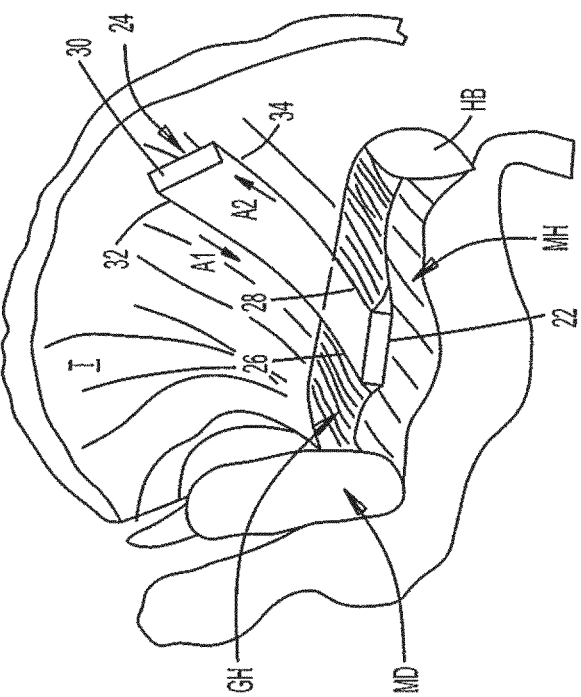
FIGS. 7A and 7B show a method of treating obstructive sleep apnea including implanting a second implant part in a tongue, in accordance with one embodiment of the present invention.
Figure 7A:
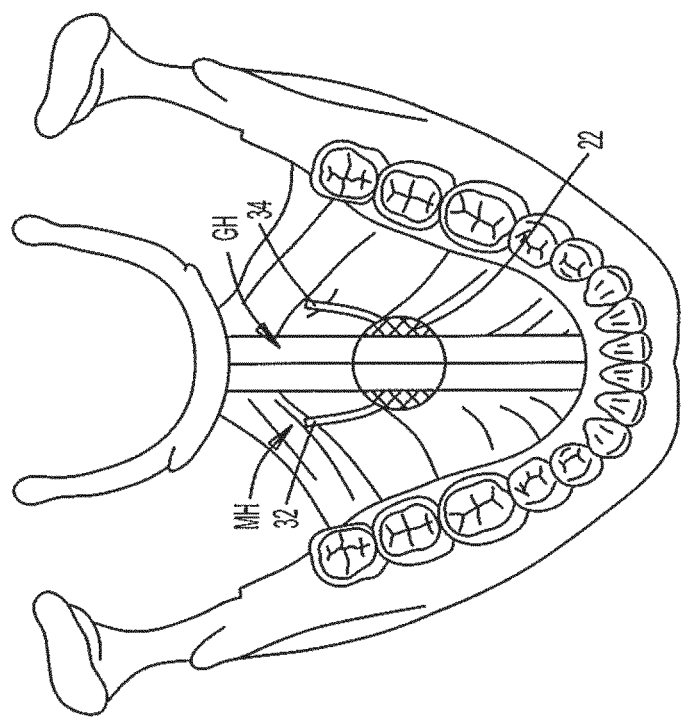

Referring now to FIGS. 7A and 7B, after the first implant part 22 has been implanted between the geniohyoid musculature GH and the mylohyoid musculature MH, and after scar tissue (e.g. a scar plane) has been allowed to form about the first implant part 22, a second implant part 24, such as that shown and described above in FIGS. 4B and 5A-C, may be connected with the first implant part 22 and/or the scar tissue that has formed around the first implant part.

The second implant part or tongue implant may be implanted by advancing first and second arms 32, 32 of the second implant part 24 in lateral directions through the rear of the tongue T until the buttress section 30 of the second implant part 24 is centered in the tongue T. Advancement of the first and second arms is preferably facilitated by attaching tissue piercing elements such as needles to the free ends of both arms. In one embodiment, a small diameter trocar is desirably advanced through the musculature and into the floor of the mouth near the base of the tongue. A snare may be introduced through the lumen of each trocar to grab the distal ends 24, 26 of the respective first and second arms 30, 32. The first and second arms 30, 32 are pulled through the trocar and the trocar is removed. The free ends 26, 28 of the first and second arms 32, 34 are desirably pulled until the back of the tongue T is advanced just enough so that it does not form a seal against the back wall of the pharynx. The first and second arms 32, 34 may be attached to the first implant part 22 and/or the scar tissue to set the tongue in the new position. In embodiments where the first implant part is resorbable and in which the scar tissue is formed without using an implant, the first and second arms may also be attached to scar tissue formed in the inframandibular region. By securing the first implant part 22 in soft tissue such as the plane between the geniohyoid GH and the mylohyoid MH muscles, the "cheese-cutter" effect found in tongue implants having hard stops (e.g. a bone anchor) is avoided. The first and second arms 32, 34 of the second implant part 24 may be attached to the first implant part and/or scar tissue using sutures, glue, toggles, ultrasonic welding, interference with barbed elements, or direct knotting of the elongated second implant part 24 with the first implant part 22 or the scar tissue.

In one embodiment, the second implant part is fabricated as a tapered hollow braided shell through which the free ends of the first and second arms are passed. Once the tongue is set into the proper position, the large end of the flexible tube is passed over the free ends of the first and second arms. The small diameter end of the tube is pushed upward in the direction of the tongue in engagement with the barbed element. As the tube collapses and the small diameter end of the tube is pressed against the large diameter end, the collapsed mass of the tube serves as a load-bearing element against the surrounding soft tissue. Although this particular embodiment is not limited by any particular theory of operation, it is believed that the above-described structure provides an infinite number of anchoring locations or points for each distal end of the first and second arms of the first part of the implant.

A surgeon may adjust the length of the respective first and second arms 32, 34 to shift the tongue T in an anterior and/or inferior direction so as to minimize the possibility of OSA episodes. The first and second arms 32, 34 may include barbs that enable the first and second arms to be advanced through the interstices or pores of the first implant part 22 and/or the scar tissue in the inframandibular region. The barbs preferably enable the arms to move more easily in the direction designated $A_1$, while providing more resistance to movement when the arms are pulled in the direction designated $A_2$.

Figure 8A:
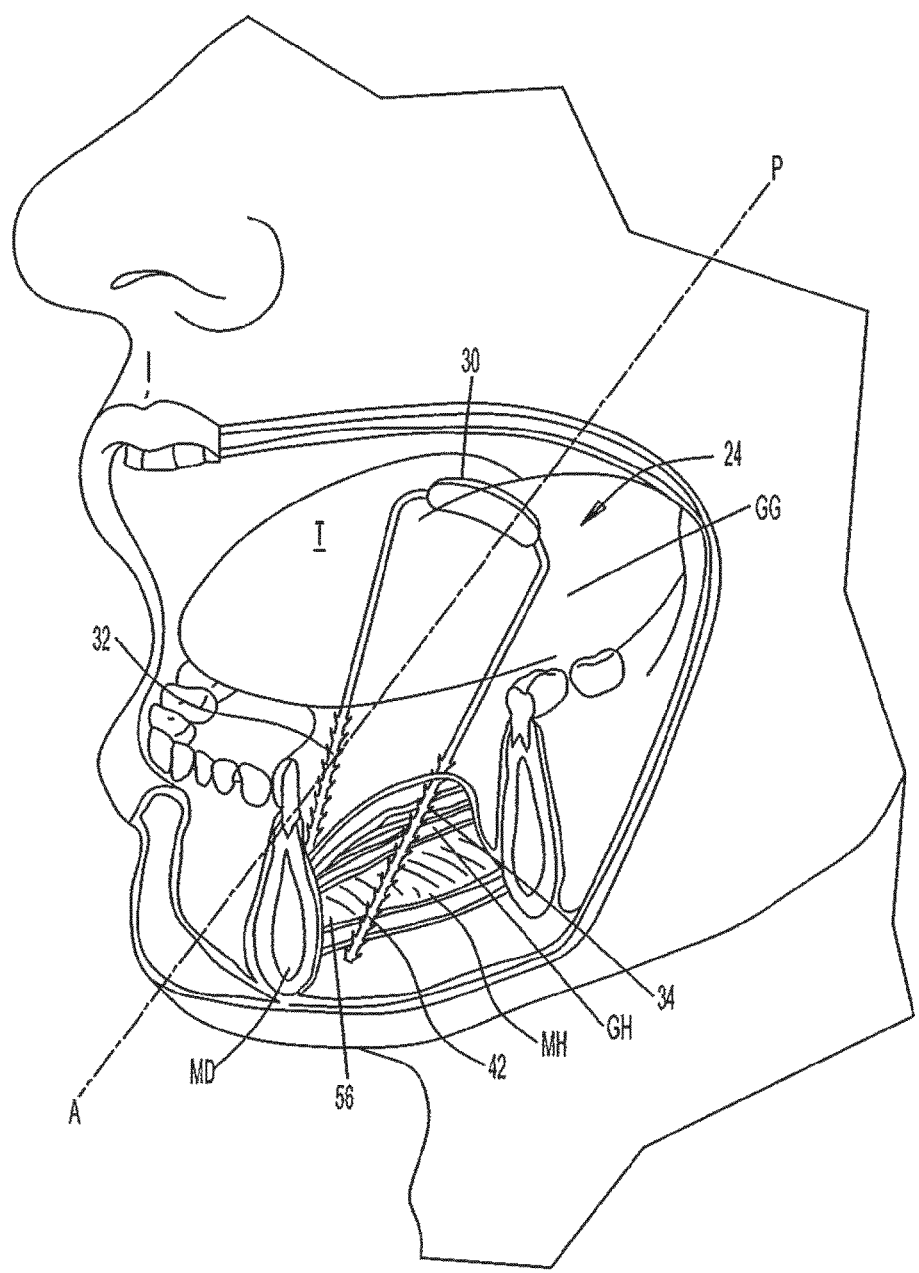
FIGS. 8A and 8B show the second implant part of FIGS. 5A-5C implanted in a tongue, in accordance with one embodiment of the present invention.
Figure 8B:
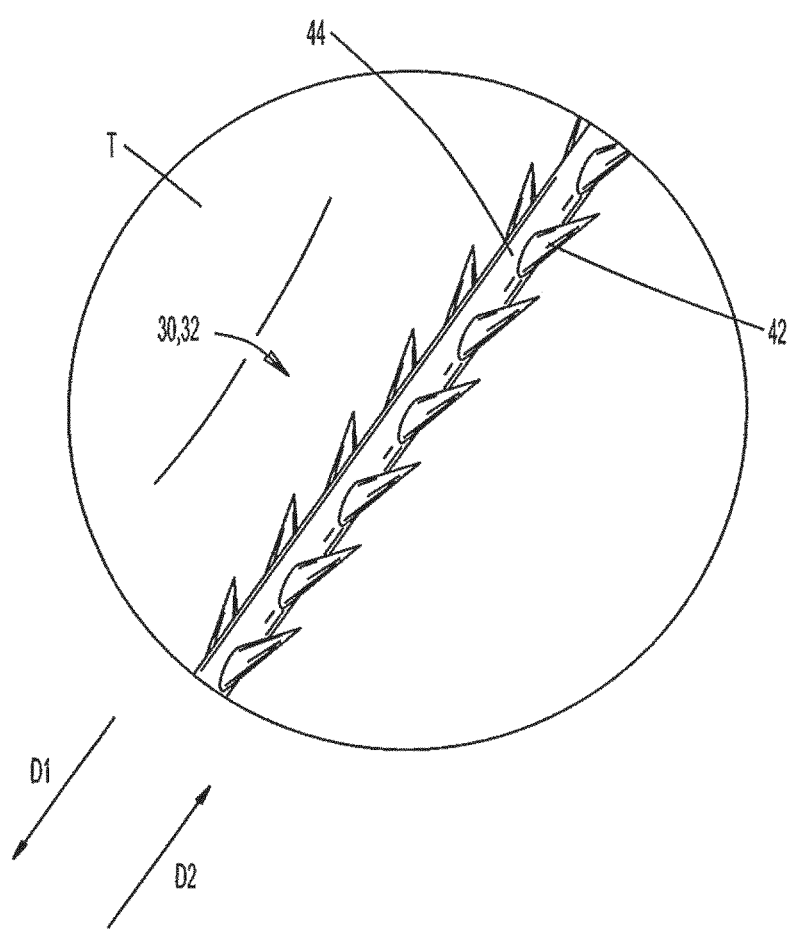

Referring to FIGS. 8A and 8B, in one embodiment, the second implant part 24 or tongue implant is preferably positioned within the tongue T so that the buttress section 30 is located in the center of the tongue body and extends laterally toward the sides of the oral cavity. The buttress section 30 extends along an axis that traverses or is substantially perpendicular with an anterior-posterior axis (designated A-P) of the tongue T, and preferably has a larger surface area than other sections of the second implant part 24 for anchoring the second implant part in place and for avoiding the "cheese cutter" effect present when using implants with immovable anchor positions (e.g. bone anchors), or implants having a relatively small diameter filament implanted in the tongue. First and second arms 32, 34 of the second implant part 24 are desirably advanced from the buttress section 30 thereof toward the anterior end 56 of the mylohyoid muscle MH.

One or more of the first and second arms 32, 34 extending through the tissue of the tongue T preferably includes a flexible core 44 and a plurality of barbs 42 projecting outwardly from the flexible core 44 as shown in FIG. 8B. The barbs 42 preferably collapse inwardly toward the core 44 as the arms 32, 34 are pulled in a first direction designated $D_1$. The barbs 42 project outwardly when the arms 32, 34 are pulled in an opposite second direction designated $D_2$ for holding the arms 32, 34 in place in the tissue of the tongue T. It is believed that the barbs 42 enhance anchoring of the second implant part 24 in tissue and enhance securing the arms 32, 34 of the second implant part to the first implant part and/or the scar tissue in the inframandibular region.

One or more barbed elements may also be placed within the core of an elongated second implant part or tongue implant, such as within the core of a braided tube, or a braided tube may be formed about one or more barbed elements. The barbs preferably project through interstices of a braided element so as to enable enhanced tissue fixation. Needles may be secured to the respective distal ends of the arms for advancing the arms through tissue, muscle, cartilage, or scar tissue, such as through the thyroid cartilage of a patient.

Referring once again to FIG. 5, in one embodiment, the center buttress section 30 of the second implant part 24 is adapted to be implanted into the base of the posterior tongue T near the oropharynyx, and the free ends of the first and second arms 32, 34 are adapted to be connected to the first implant part 22 and/or scar tissue disposed in the inframandibular region. As noted above, the center buttress section 30 of the second implant part 24 is desirably expanded at the point that is implanted in the tongue.

Figure 9:
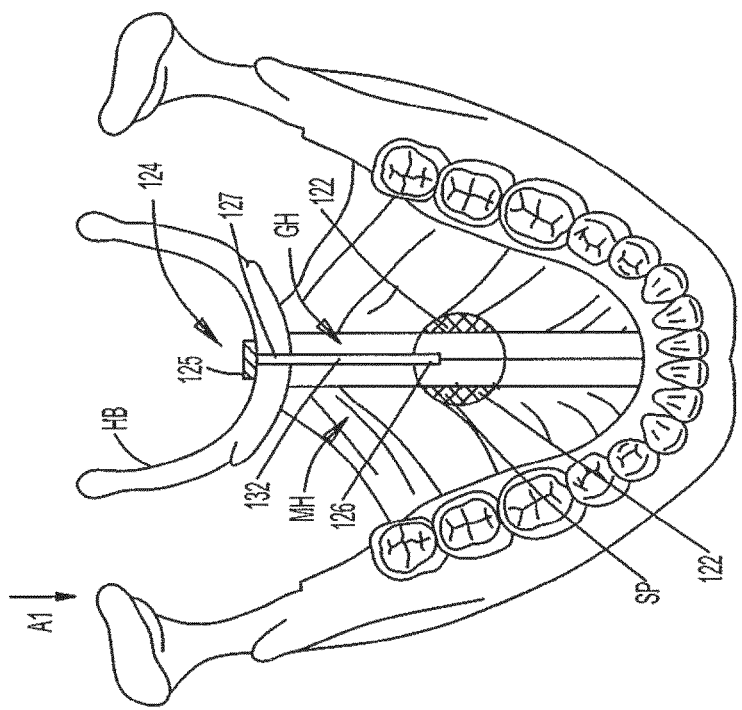
FIG. 9 shows an implant system for treating obstructive sleep apnea, in accordance with one embodiment of the present invention.

FIG. 9 illustrates another system for treating OSA that includes a first implant part or anchoring element 122 implanted in an inframandibular region of a head such as being disposed between geniohyoid musculature GH and mylohyoid musculature MH. The first implant part 122 may be a flexible or compliant biocompatible mesh or fabric that desirably precipitates the formation of scar tissue or a scar plane SP about the first implant part 122. A sclerosing agent may be used with the first implant part to encourage the growth of scar tissue. After implantation between the geniohyoid musculature GH and the mylohyoid musculature MH, the first implant part 122 is preferably left in place as the scar tissue forms about the first implant part 122. The first implant part may be resorbable as the scar tissue forms. A second implant part 124, such as a second implant part having one or more of the features shown in FIGS. 5A-5C, may be coupled with the hyoid bone HB of a patient. The second implant part 124 desirably includes an anchor 125, and a tether 132 having an anterior end 126 coupled with the first implant part 122 and a posterior end 127 coupled with the anchor 125. The tether 132 may include barbs for attaching the tether 132 to the first implant part 122 or scar tissue. The length of the tether 132 may be adjusted for advancing the hyoid bone HB in the anterior and/or inferior direction designated $A_1$. As the hyoid bone HB is moved in the anterior and/or inferior direction designated $A_1$, the posterior surface of the tongue is preferably shifted anteriorly and/or inferiorly for spacing a posterior surface of the tongue from an opposing pharyngeal wall for minimizing the likelihood of OSA events.

Figure 10:
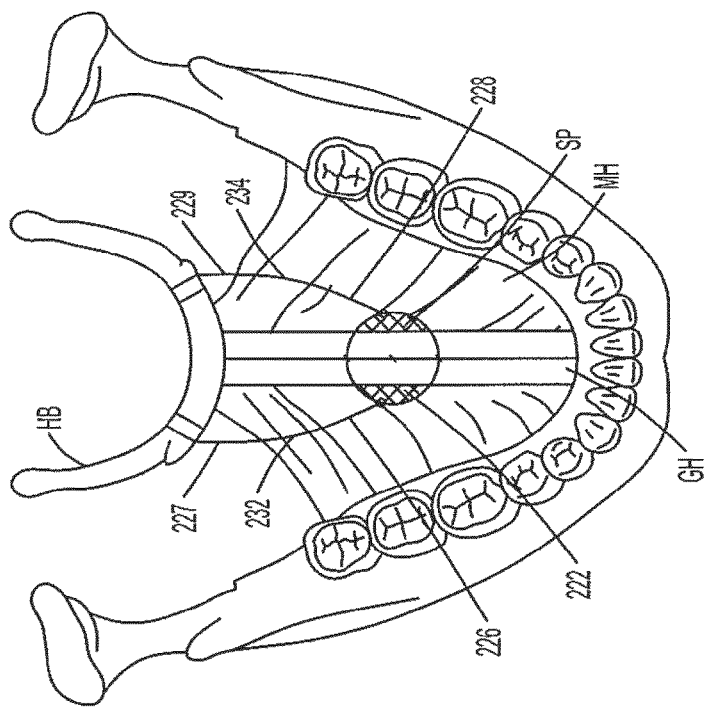
FIG. 10 shows an implant system for treating obstructive sleep apnea, in accordance with one embodiment of the present invention.

Referring now to FIG. 10, another system for treating OSA desirably includes a first implant part 222 or anchoring element, such as flexible mesh or porous fabric, implanted between geniohyoid musculature GH and mylohyoid musculature MH. After implantation of the first implant part 222, the first implant part is maintained between the geniohyoid musculature GH and the mylohyoid musculature MH so that a scar plane SP may form about the first implant part 222. After the scar plane SP has been formed, tethers 232, 234 may be used for coupling the scar plane with a hyoid bone HB. The first tether 232 desirably has an anterior end 226 attached to the first implant part 222 and/or scar tissue, and a posterior end 227 coupled with the hyoid bone HB. The posterior end 227 of the first tether 232 is wrapped around the hyoid bone HB at least once. Preferably, the posterior end 227 of the first tether 232 is wrapped around the hyoid bone HB multiple times. The implant system also includes the second tether 234 having an anterior end 228 attached to the first implant part 222 and/or scar tissue, and a posterior end 229 anchored to the hyoid bone HB. As above, the posterior end 229 of the second tether 234 is desirably wrapped around the hyoid bone HB one or more times.

FIGS. 11-12 illustrate yet another embodiment of an implant system to treat OSA. The implant system 1100 includes a ribbon-like element or loop 1105 of a suitable, flexible, non-resorbable material such as expanded polytetrafluoroethylene (ePTFE) that is implanted within the tongue in a manner similar to that described above. The ribbon-like element preferably has a length of approximately 20-60 cm, and more preferably approximately 30-45 cm. The cross-section of the ribbon-like element 1105 preferably includes a major axis 1101 and a minor axis 1102 as shown in FIG. 11B. In a preferred embodiment, the major axis is approximately 2-5 mm and the minor axis is approximately 1-3 mm. If the ribbon-like element is made of ePTFE, the internodal distances within the ePTFE are preferably 10-100 microns. The cross sectional area of the ribbon-like element is preferably substantially constant along its length. Other materials suitable as the ribbon-like element include polyethylene terephalate, polypropylene, polycarbonate, polyurethane, silicone, silicon, nitinol, and 316C stainless steel.

Figure 12A:
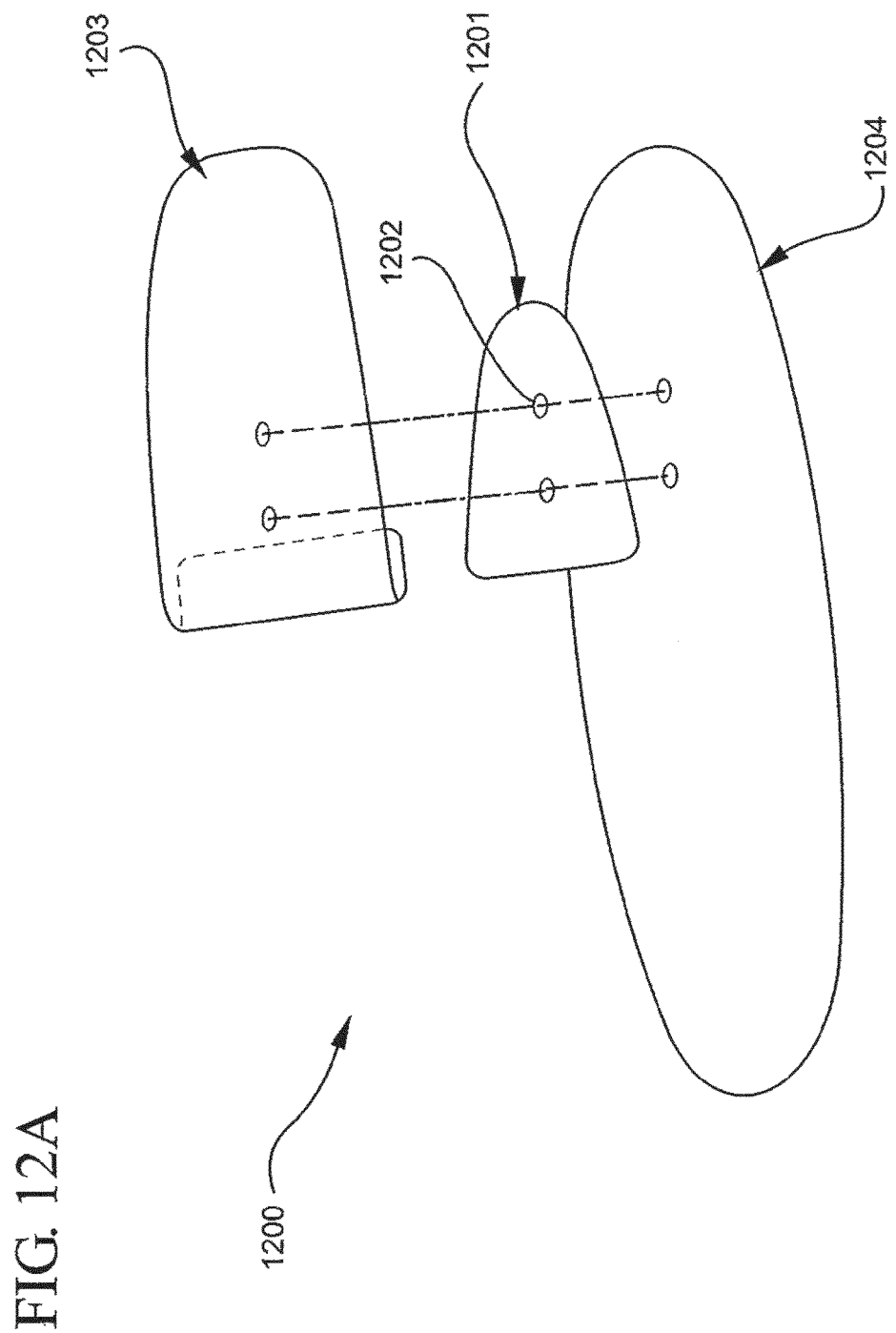
FIGS. 12A-12B illustrate one embodiment of a first implant that can be used with the ribbon-like element of FIGS. 11A-11B.
Figure 12B:
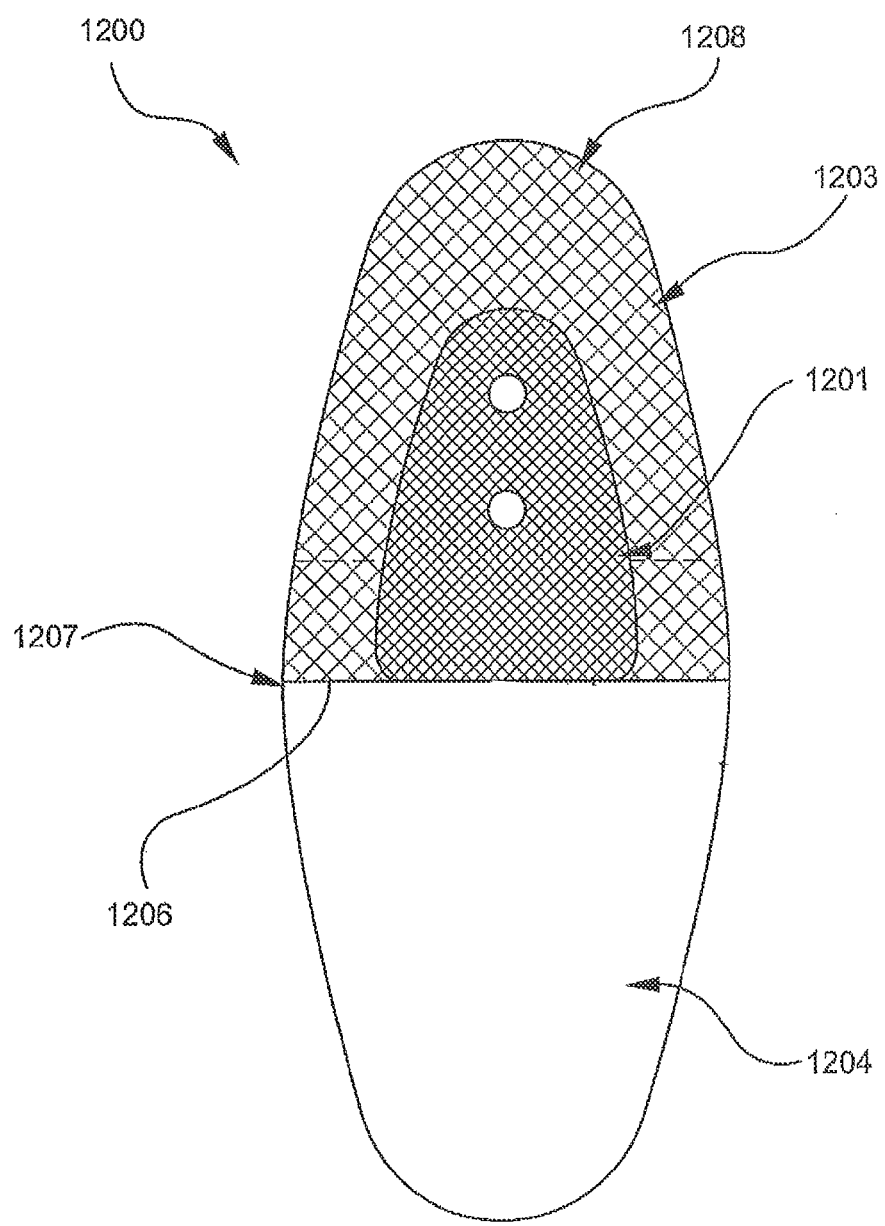

FIGS. 12A and 12B illustrate one embodiment of the first implant element 1200 of the implant system 1100 that may incorporate the ribbon-like element 1105 of FIGS. 11A and 11B as will be described in more detail below. The first implant 1200 is preferably comprised of a biocompatible mesh cover 1203, a mesh base 1204, and a relatively solid anchor 1201 that is preferably comprised of a biocompatible non-resorbable material such as silicon, polyurethane, polypropylene, polyethylene, stainless steel, nitinol, tantalum, or titanium. The term relatively solid means that the anchor has a stiffness greater than that of the ribbon-like element, and thus, the anchor may also be comprised of a thicker mesh material, or a resorbable material provided that it is a material that resorbs at a rate that allows for adequate tissue ingrowth. The anchor 1201 has at least one hole 1202 therethrough so as to allow first and second ends 1110, 1112 of the ribbon-like element to be passed through and secured to the first implant. The diameter of the holes 1202 in the anchor 1201 are preferably from 1-7 mm, but will depend on the size of the ribbon-like element.

As illustrated in FIG. 12B, the anchor 1201 is preferably placed within an open space or pouch 1206 formed between the mesh cover 1203 and mesh base 1204 by the manner in which they are secured to one another. The pouch 1206 is preferably created by forming a crease 1207 in the mesh cover 1203 and then suturing or welding the mesh cover to the mesh base together at the crease 1207. If sutures are used to close the pouch edges 1208, they are preferably non-resorbable. Alternatively, the pouch edges 1208 can be welded together. Welding can be accomplished by ultrasonic welding or laser welding. Although one particular shape and configuration is shown for the anchor, those skilled in the art will readily understand that other configurations and shapes, such as rectangular, square, triangular or round, may also be suitable. In addition, the mesh cover 1203 and base 1204 can be secured to one another without forming a crease in the mesh cover. Instead, the two mesh components can be secured together by welding, suturing, sewing, riveting or the like.

Figure 13A:
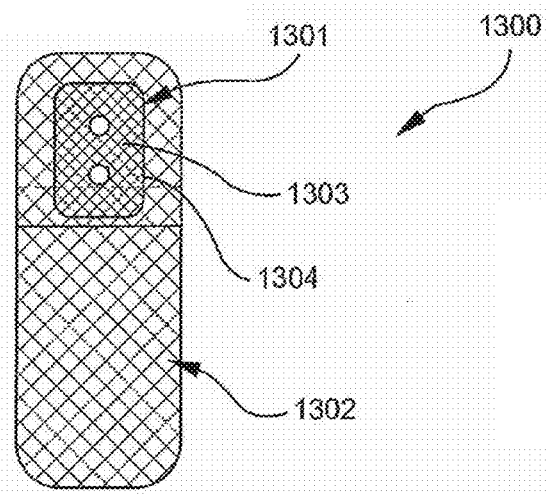
FIGS. 13A-13E illustrate alternate embodiments of the first implant of FIGS. 12A-12B.
Figure 13B:
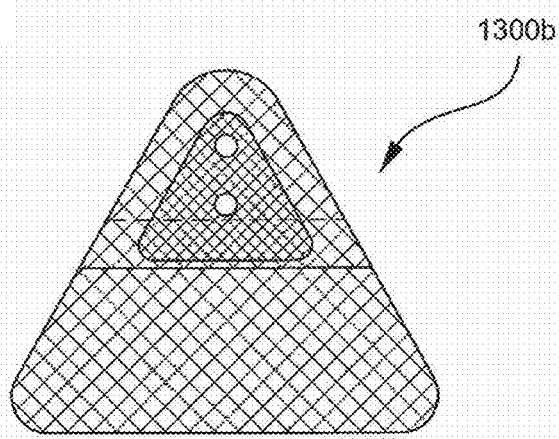
Figure 13C:
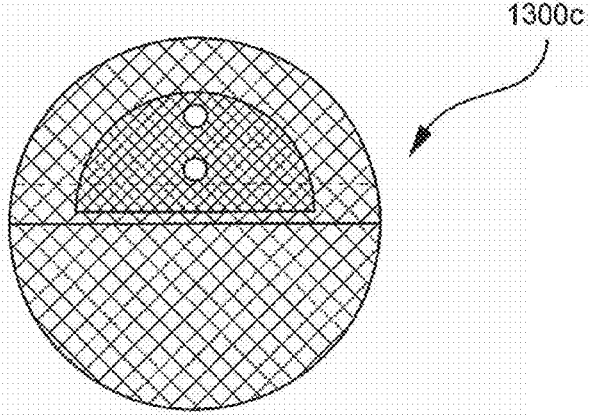
Figure 13D:
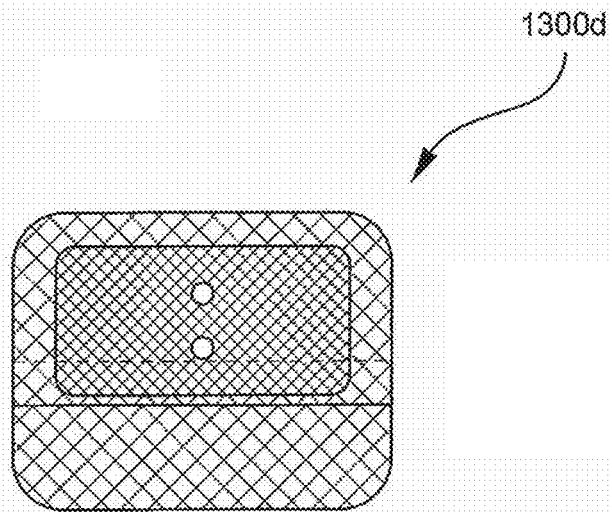
Figure 13E:
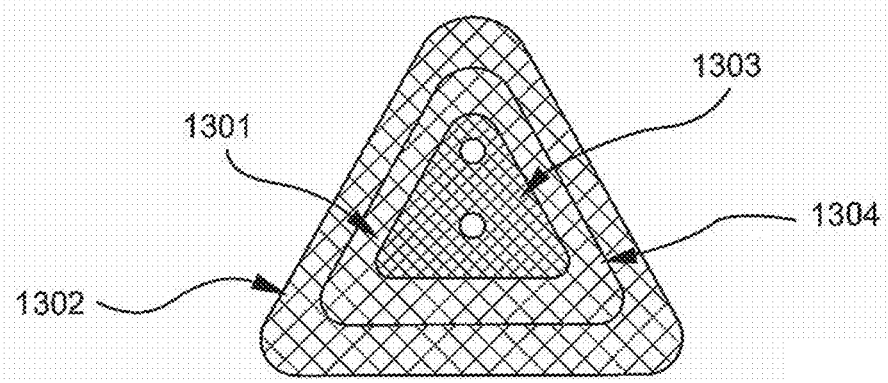
Figure 14:
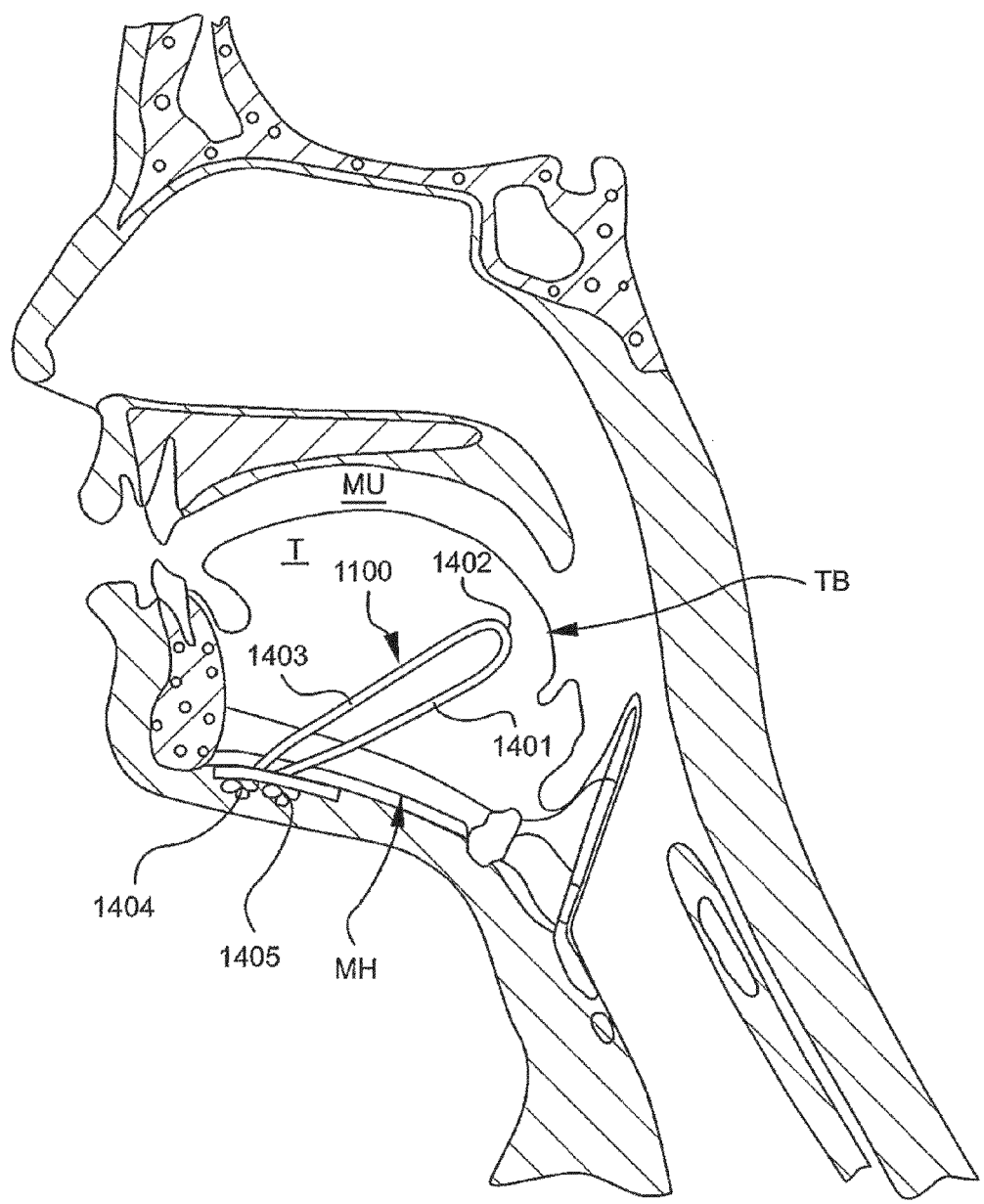
FIG. 14 illustrates an implant such as that shown in FIGS. 11-12 implanted in the body.

In addition, the overall shape of the first implant may also vary. FIGS. 13A-E illustrate exemplary alternative configurations that may be used for the first implant. FIG. 13A illustrates a rectangular configuration of the first implant 1300 comprising a mesh cover 1301, a mesh base 1302, an anchor 1303 with holes 1304 therethrough to receive the ribbon-like tongue implant. FIGS. 13B-D illustrate triangular (13B), round (13C), and square (13D) versions of the first implant 1300b, 1300c, 1300d respectively. FIG. 13E illustrates how the mesh cover 1301 is sutured over the anchor 1303 so as to secure the mesh cover 1301 to the mesh base 1302. The suture 1304 is illustrated around the periphery of the mesh cover 1301. An exemplary implant 1100 implanted in the body is illustrated in FIG. 14.

In one embodiment, the first implant is shaped to closely contour the interior surface of the mandible at the level of the mylohyoid muscle. This shape allows the surgeon to secure the first implant with sutures or clips to dense connective tissue near the mandible and avoid suturing into muscle. The first implant can be supplied as a generally triangular shaped member that is larger than the mandible dimensions and trimmed to size by the surgeon at the time of implantation. Alternatively, the first anchor can be supplied in various sizes that fit a variety of human inframandibular spaces.

Figure 16:
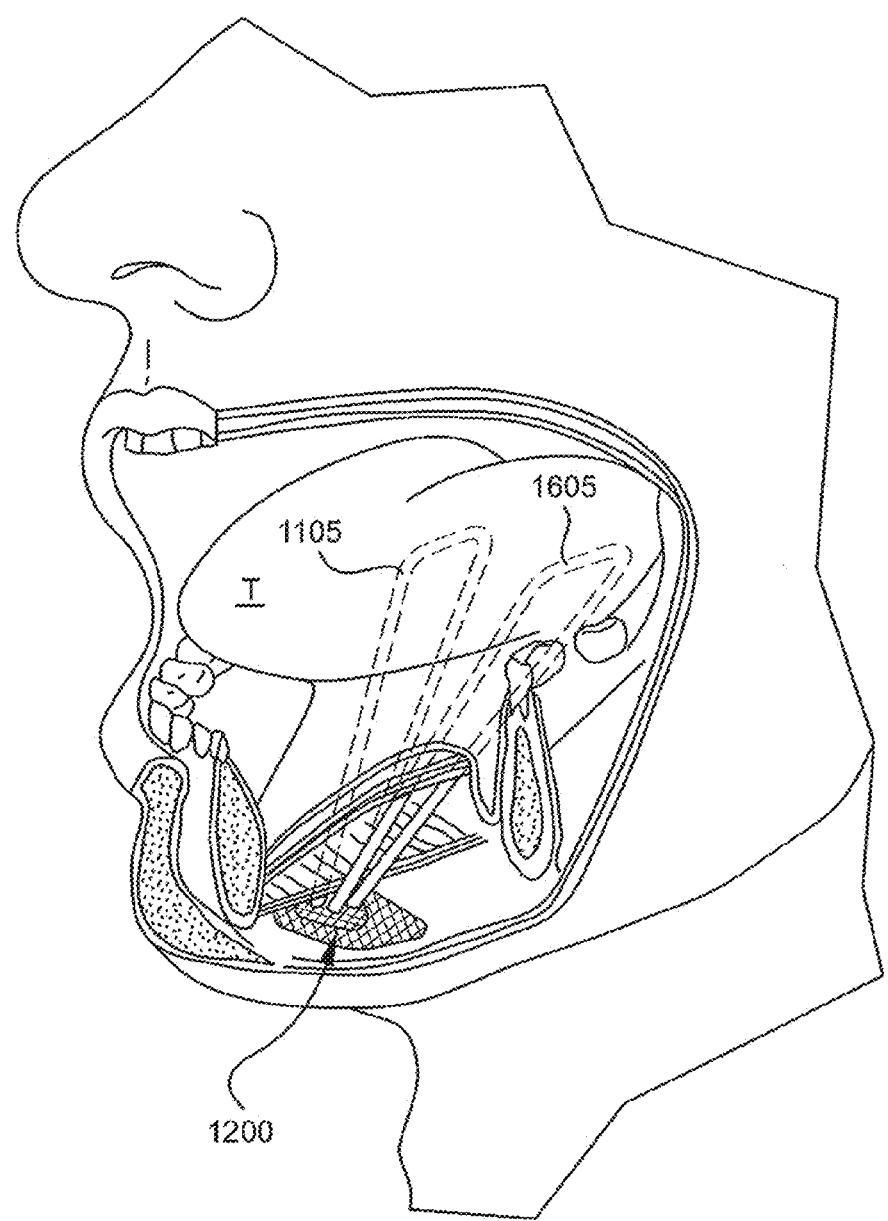
FIG. 16 illustrates an exemplary implant including first and second ribbon-like elements implanted in the body.

In an alternate embodiment, the implant system includes a second ribbon-like element 1605 as shown in FIG. 16. The second ribbon-like element is similar in shape and construction to the first ribbon-like element described above. The first and second ribbon-like elements enable a "double loop" procedure where both loops are implanted across the median sulcus at the base of the tongue as illustrated. With two ribbon-like elements, different regions on the tongue base can be engaged for suspension. The distance between the first and second ribbon-like elements in the base of the tongue can range from 1-20 mm, depending on the size of the tongue, the site of obstruction, and the severity of apnea. Alternatively, each of the first and second ribbon-like elements are implanted beneath the mucosa of the tongue base in an anterior-posterior configuration, i.e., neither of the implants cross the median sulcus. The first and second implants are pulled with a looped suture from one of these holes and then beneath the submucosa to the other hole. In both of these "double loop" procedures, the anchor 1601 portion of the implant 1600 in the mandible will have at least two holes, preferably four holes, to allow both the first and second ribbon-like elements to be anchored thereto.

The tongue anchor and first (and optionally second) ribbon-like elements may be combined with surgical tools to form a kit to conduct the implantation. The kit 1500 may include the first implant 1501 used to form an inframandibular anchor, at least one ribbon-like element 1505 to be placed in the tongue, at least one inserter or trocar 1503 and an optional stylet 1504 adapted to be placed through the patients tongue, at least one snare 1506 adapted to be placed through the trocar and capable of snaring the ribbon-like element, at least one looped suture 1508 to pull the tongue implant below the mucosa and across the tongue midline, and one or more sutures 1507 to facilitate anchoring of the first implant to tissues near the mandible and closing the skin and fascia. In one embodiment, the trocar, stylet, and snare can be replaced with a surgical awl such as those used to pass wires in orthopaedic surgery.

Figure 15:
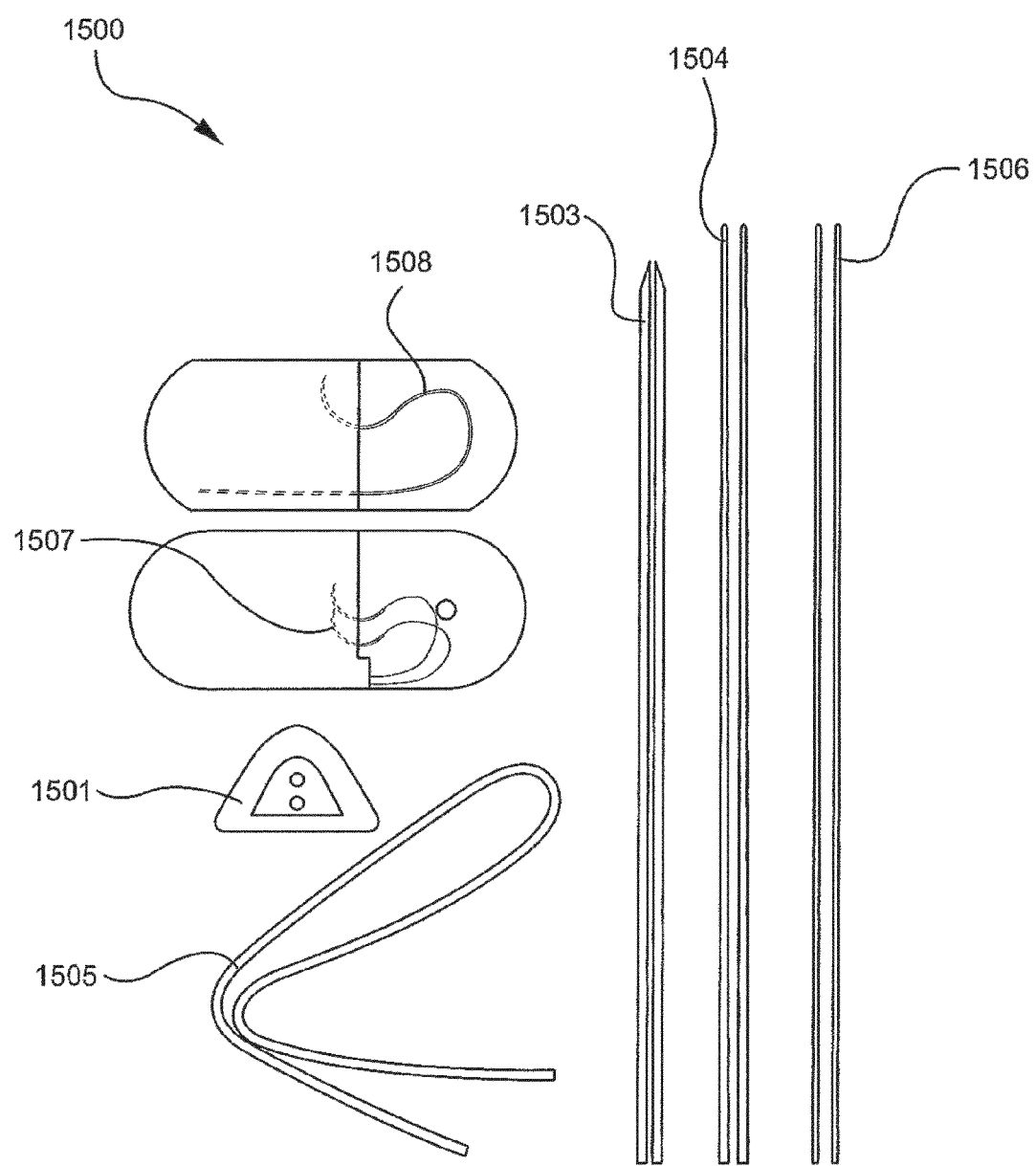
FIG. 15 illustrates an exemplary kit according to the present invention.
Figure 17A:
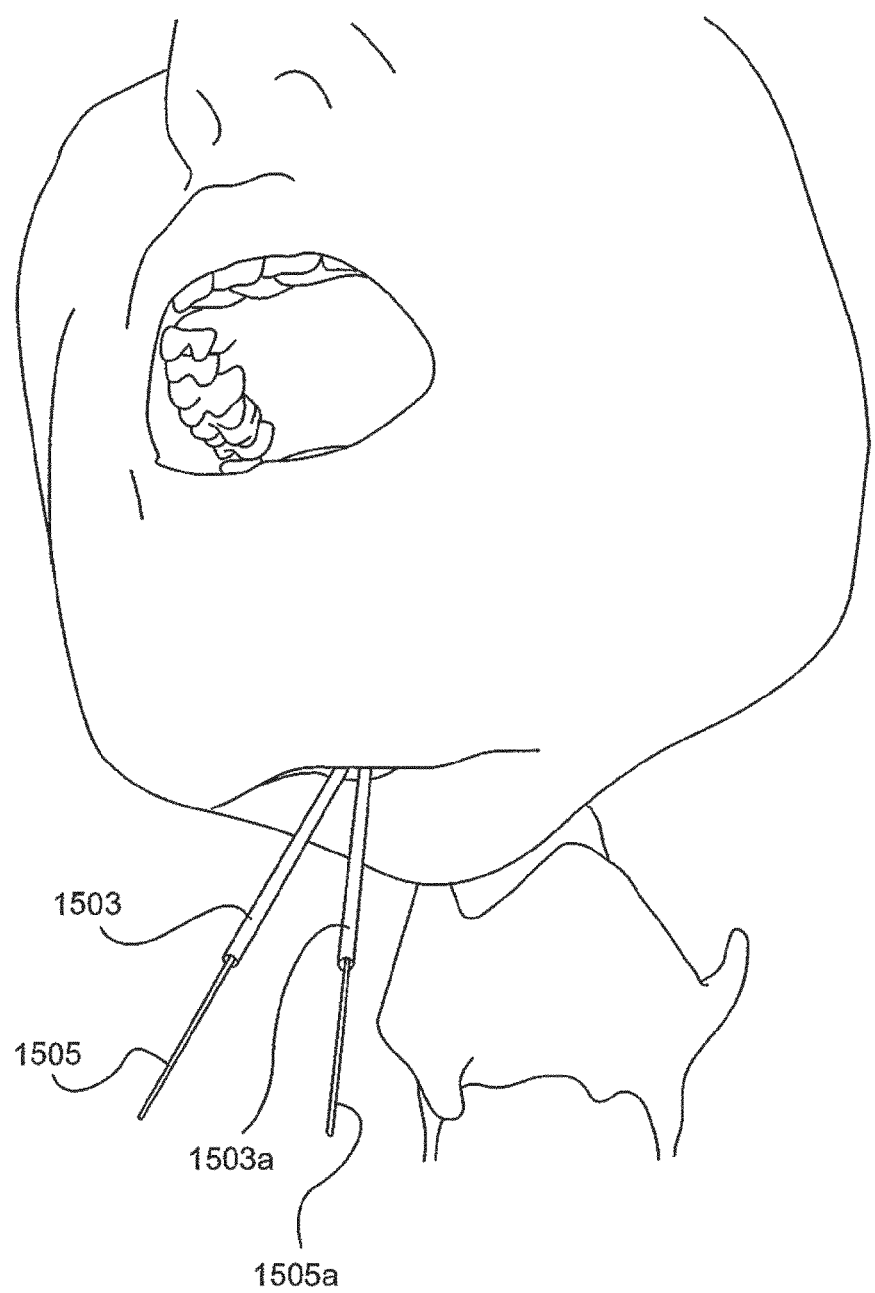
Figure 17B:
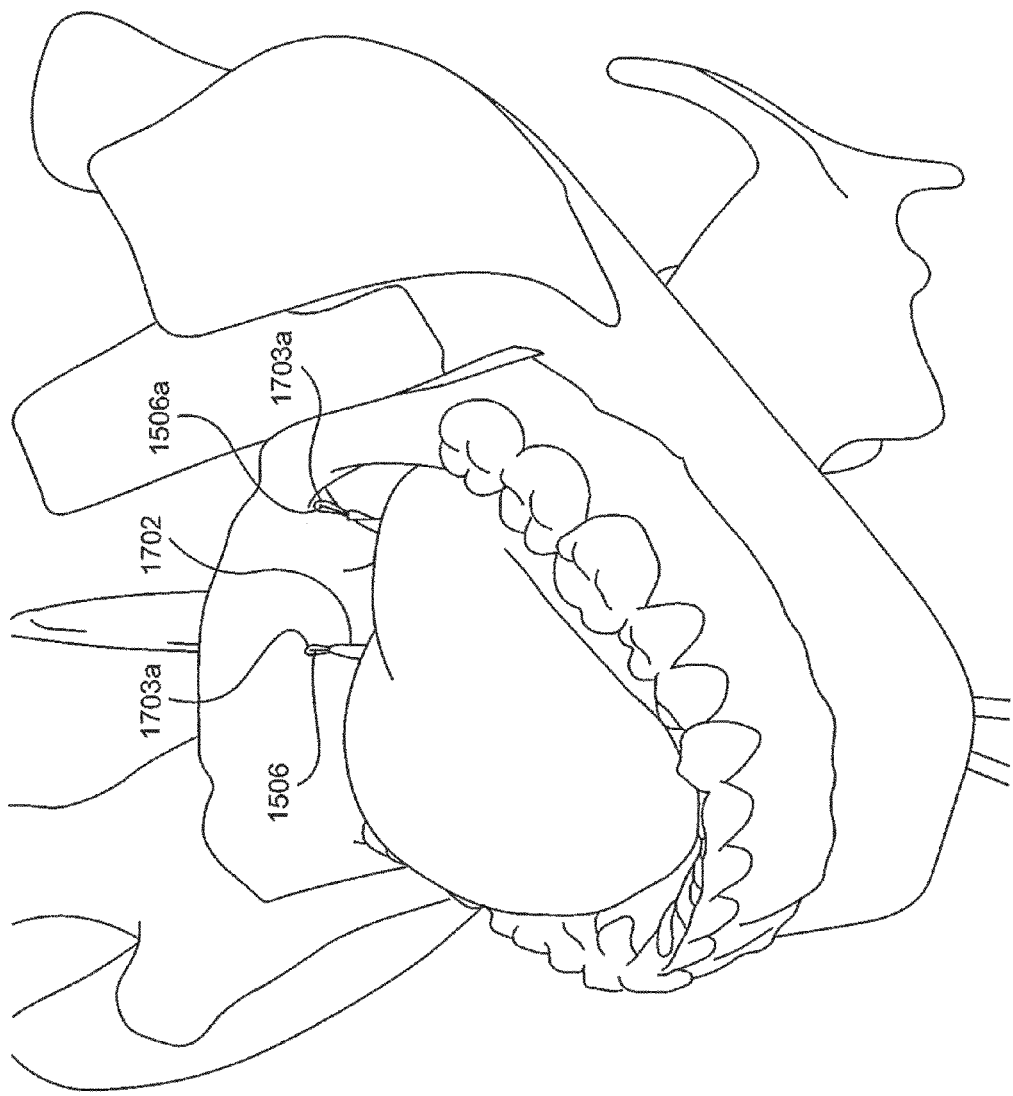

Referring specifically to the implant system described above and illustrated in FIGS. 11 and 12, the patient is first prepared for surgery using general anesthesia and endotracheal intubation. A submental full thickness incision is made through the skin and subcutaneous tissue (i.e., perpendicular to midline of mylohyoid muscle) approximately 2-4 cm in length to expose digastrics and mylohyoid muscles. An incision may also be made through the midline of the mylohyoid muscle to visualize the midline of the paired bellies of the geniohyoid muscles. The first implant 1105 is placed over the mylohyoid muscle and used as a template for marking the trocar entry sites. The position of holes is marked with a sterile marking pen and the anchor removed from the incision. A trocar or obturator 1503 such as shown in FIG. 15, is inserted through the mylohyoid muscle (avoiding the geniohyoid muscle) and directed towards the base of the tongue so the tip 1702 of the trocar exits 0.5-1.0 cm from median sulcus at a location between the circumvallate papillae and lingual tonsils as shown in FIGS. 17*a-b*. It may be necessary to place a small incision in the mylohyoid between the two marked points to allow for visibility and retraction of the geniohyoid muscles. A stylet 1505 is removed from the trocar and a snare 1506 passed through the trocar so that it exits at base of tongue as shown in FIG. 17*b*. A second trocar 1503*a* and snare 1506*a* will be passed as described through the other side of the tongue.

Approximately 1-2 cm of the ribbon-like element 1105 is inserted into the loop 1703*a* of the snare 1506*a* as shown in FIG. 17*c*, and pulled through the channel previously created in the tongue by the trocar in the direction indicated by the arrow. The ribbon-like element is then pulled through the tongue so that approximately 5-10 cm of the loop is visible in the inframandibular region. A sterile apron may be applied in this region to allow for the loop to remain sterile.

Figure 17D:
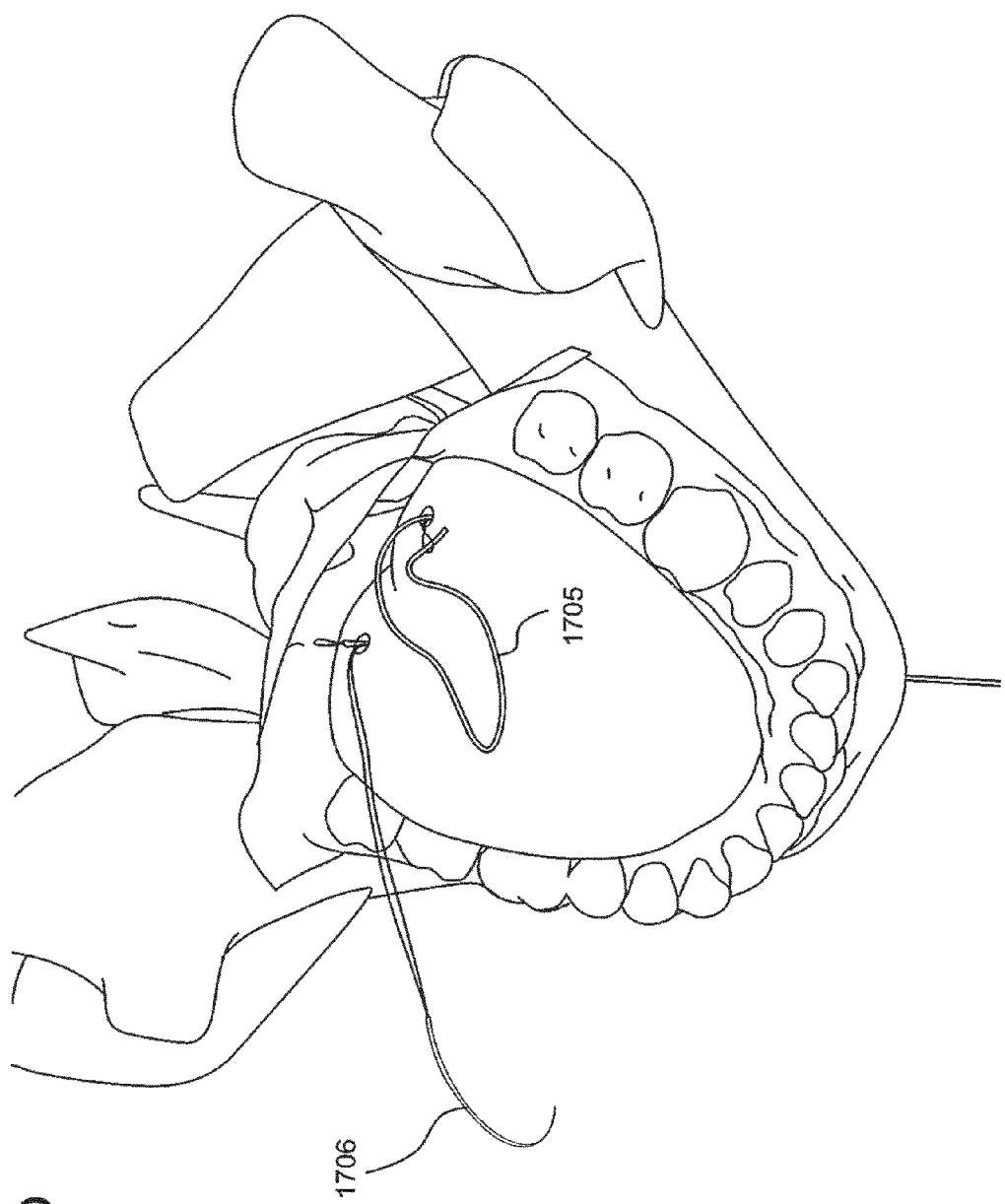
Figure 17E:
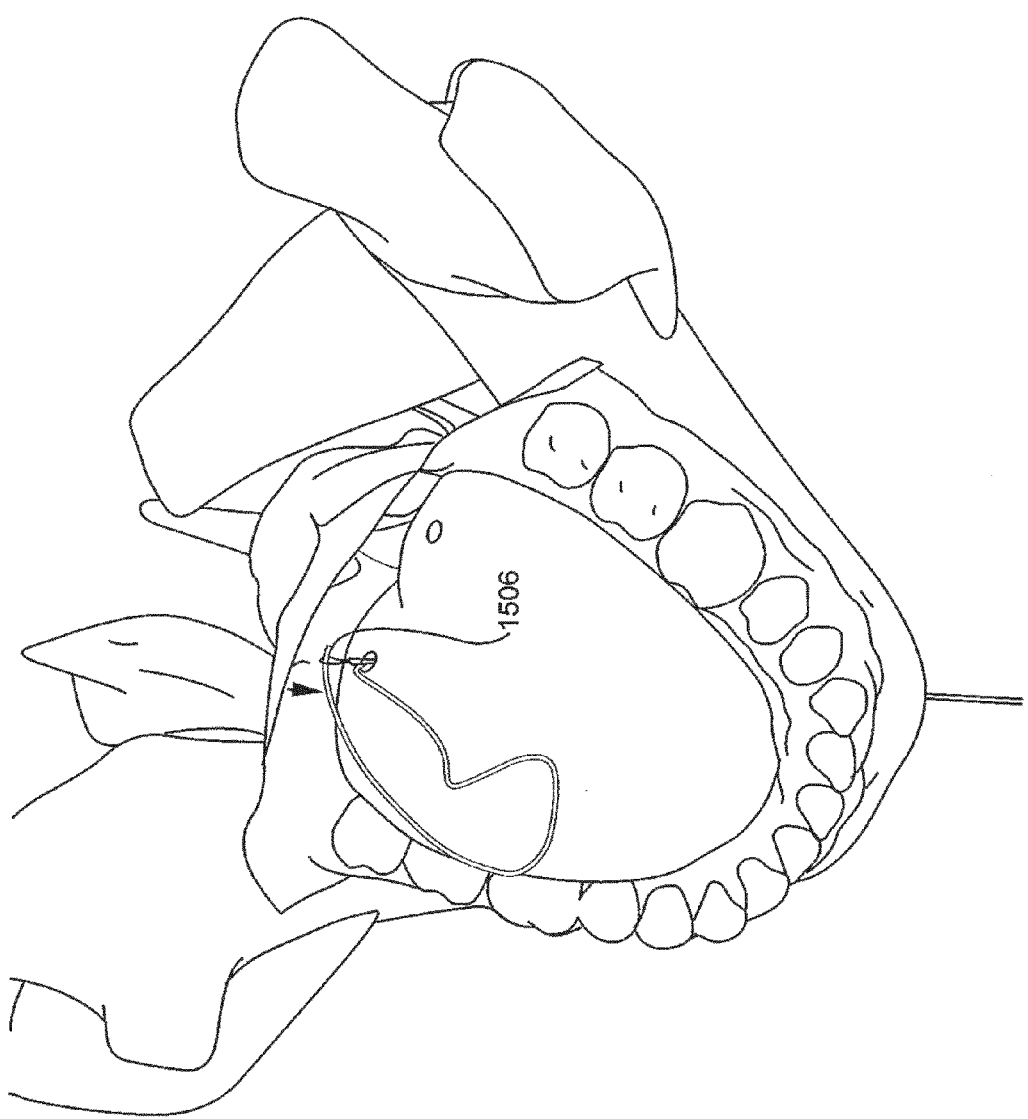

A looped suture 1705 with curved needle 1706 is then used as a snare to pull the ribbon-like element 2-5 mm below the mucosa of the tongue to the point where the snare on the other side of the median sulcus exits as shown in FIG. 17*d*. Approximately 1-2 cm of the free end of the ribbon-like element will be grabbed by the snare 1506 and used to pull the remainder of it through the tongue in the direction of the arrow in FIG. 17*e* so that it exits outside the mylohyoid muscle.

Both ends of the ribbon-like element are then pulled through the holes in the solid anchor of the first implant and the first implant is slid over both ends of the ribbon-like element until it lies against the mylohyoid muscle.

The first implant 1200 is then secured to the mylohyoid muscle and surrounding tissue near the mandible with sutures (preferably Vicryl Plus® sutures, size 3-0 or 4-0, manufactured and sold by Ethicon, Inc. of Somerville, N.J.) using a continuous suture pattern. Tension is then applied to both ends 1110 and 1112 of the ribbon-like element to remove any slack in the ribbon that may exist. The amount of tension placed on the ribbon-like element and the degree to which the base of tongue is advanced away from the posterior pharyngeal is determined by the surgeon and is typically based on patient anatomy, severity of disease, and surgeon experience.

Figure 17F:
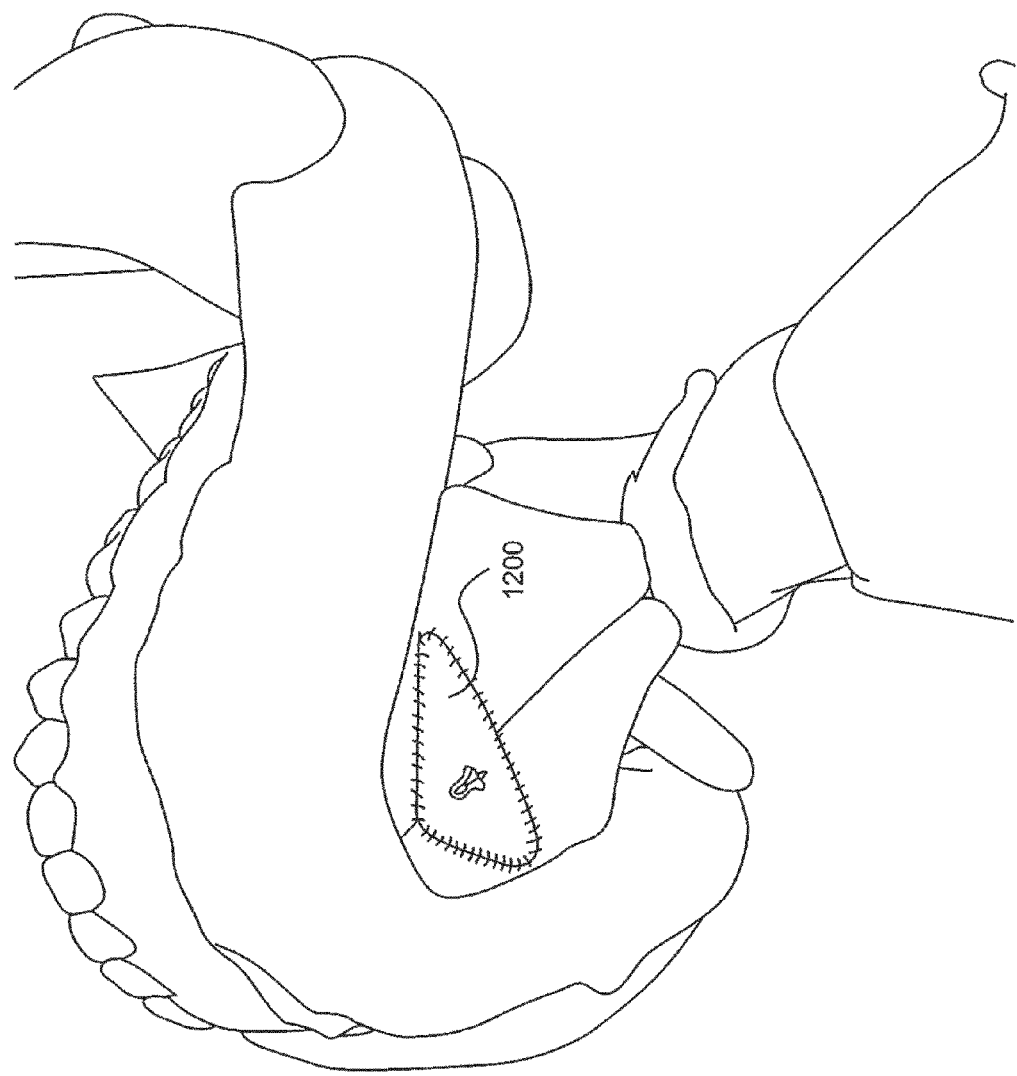

The ends 1110, 1112 of the ribbon-like element 1105 are then secured against the anchor by any suitable means, such as by knotting the ends together as shown in FIG. 17*f*. Any excess is then cut away and discarded. The subcutaneous tissue and skin are then closed with suture (preferably Monocryl® suture, size 3-0 or 2-0, also manufactured and sold by Ethicon, Inc.). The skin is closed with a Monocryl Suture (size 3-0 or 4-0), and possibly also a cyanoacrylate adhesive.

FIG. 14 illustrates the position of the implant system 1100 following the surgical procedure described above. The ribbon-like element 1401 is shown in the tongue T of the patient, with a central portion 1402 positioned several millimeters below the mucosa MU of the tongue base TB. The geometric dimensions of the central portion 1402 preferably do not differ substantially from geometric dimensions of the remainder of its length. As illustrated, the ribbon-like element extends down through the tongue T and is passed through the holes 1404 placed in the first implant 1405 located on the surface of the mylohyoid muscle MH. In this particular illustration, the ends 1110, 1112 of the loop 1404 are attached to one another by knotting. Other means for attaching the ends of the loop to the first implant are stapling, crimping, welding, and gluing.

Figure 18A:
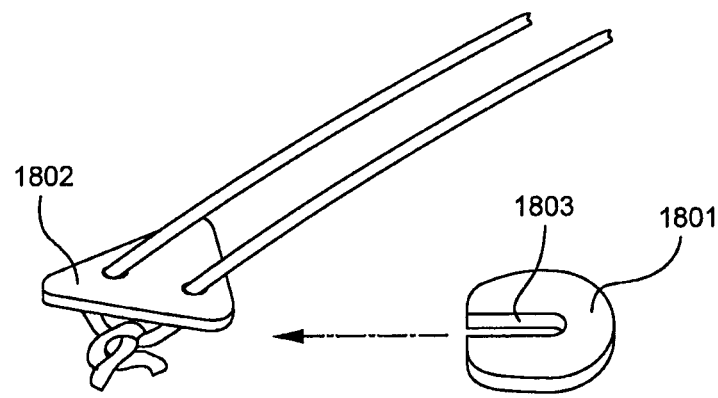
FIGS. 18a-b illustrate an exemplary adjustment element according to the present invention.
Figure 18B:
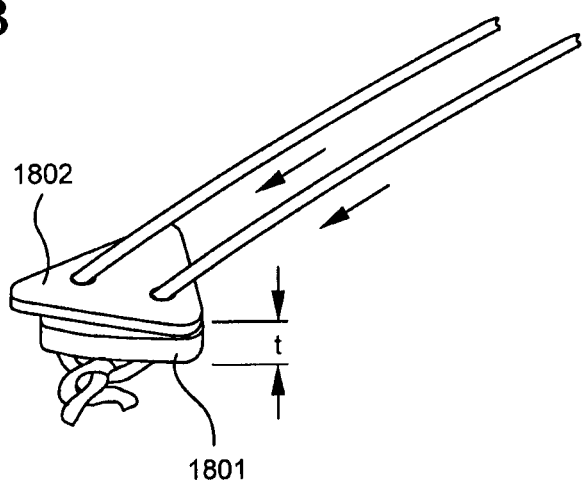
Figure 19:
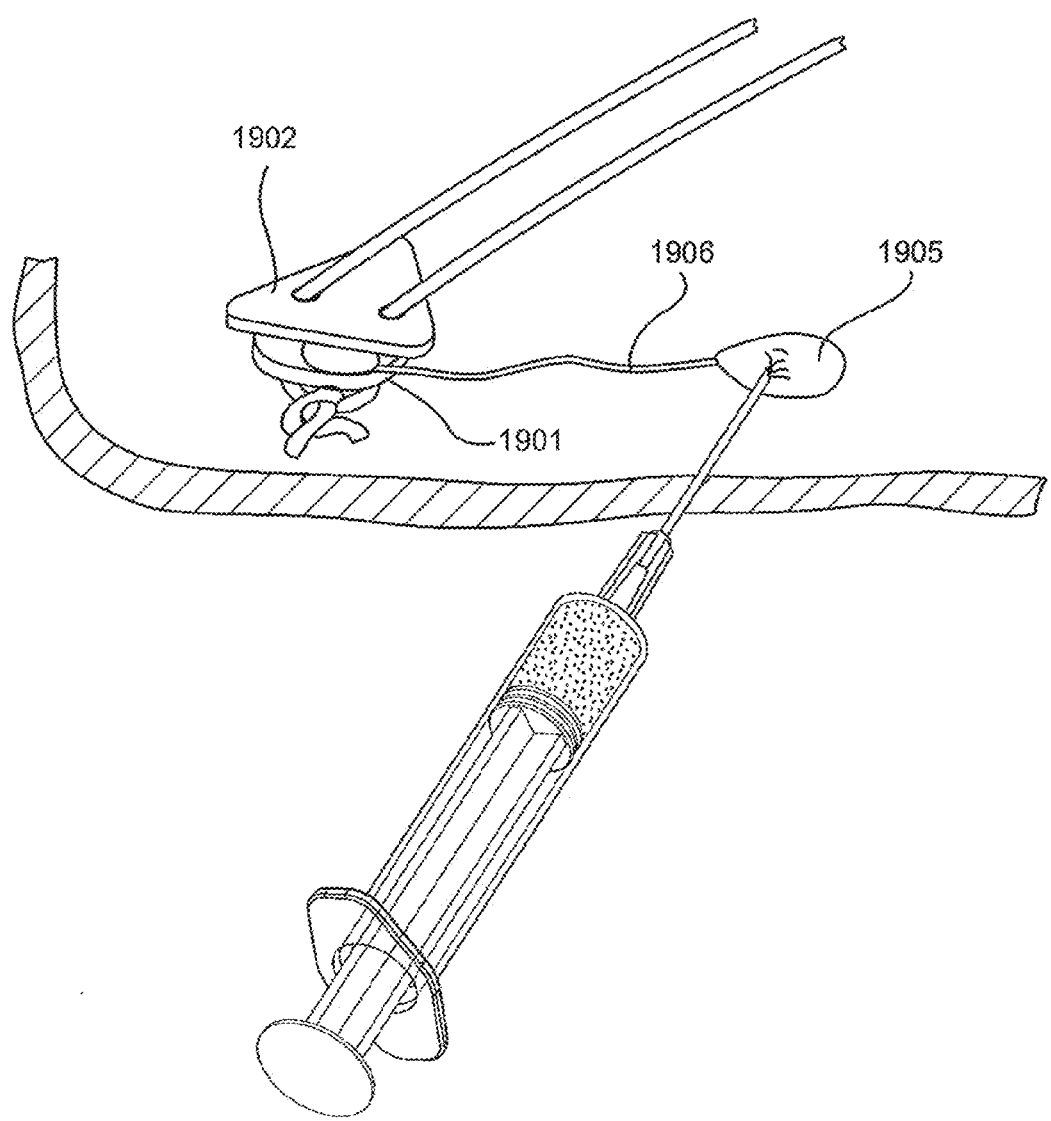
FIG. 19 illustrates an alternative adjustment element according to the present invention.

The surgeon may choose to apply a certain amount of tension on the ribbon-like element that is based on the surgeon experience, the patient anatomy, and the severity of the apnea. If there is a need to adjust the tension following surgery, the surgeon can create a small incision in the skin beneath the jaw to expose the knotted portion of the ribbon-like element. The knot can be untied and the tension reset by knotting again at the desired tension or using clips, staples or the like to connect the ends of the ribbon-like element. FIGS. 18*a-b* illustrate a small washer 1801 preferably made from a material similar to the anchor 1802 that can be slid underneath the knot to increase tension. The increase in tension will result in the base of the tongue being pulled further away from the posterior pharyngeal wall. The washer preferably has a thickness of about 1-5 mm, and at least one opening 1803 therein within which the ends of the ribbon-like element may be received. One or more of these washers can be added to the kit or can be acquired separately. In another embodiment shown in FIG. 19, a small balloon or the like 1901 can be placed between the knot and the anchor 1902. The volume of the balloon, and therefore the tension on the implant element, can be adjusted by transdermally injecting the balloon with sterile saline, water, or other biocompatible fluid after implantation. Alternatively, a separate reservoir 1905 can be injected, which may be a distance of 1-10 cm away from the balloon 1901 itself. The reservoir 1905 is fluidly coupled to the balloon 1901 by a tube 1906 that preferably has a one-way valve in it so as to maintain pressure in the balloon. In this manner, an incision would not have to be made to adjust tension on the ribbon-like element. If necessary, the filling reservoir 1905 can be squeezed or pressed by the patient or physician to drive fluid into the balloon 1901.

Techniques well known to those skilled in the art may also be used for forming scar tissue in the inframandibular region, such as laser energy, heat energy, or a sclerosing agent. An implant such as a tongue implant may be coupled with the scar tissue for shifting the position of the tongue for minimizing OSA events. A hyoid bone may also be coupled with the scar tissue using one or more elongated elements such as a tether.

The devices described above provide a number of advantages over prior art methods and devices used for treating obstructive sleep apnea syndrome and hypopnea. First, the systems, devices and methods disclosed herein provide simple surgical procedures that are minimally invasive that typically may be utilized during an outpatient procedure. In addition, the systems, devices and methods disclosed herein provide both immediate and long term results for treating obstructive sleep apnea syndrome and hypopnea, and do not require a significant level of patient compliance.

Significantly, the devices and methods described herein do not anchor the posterior aspect of the tongue to a fixed, hard structure. Rather, a "soft anchor" is used in the inframandibular region, which is significantly less likely to affect swallowing or speech, thereby providing a great improvement over prior art devices, systems and methods. The above-described devices also avoid the "cheese-cutter" effect found with prior art implants by teaching, inter alia, the use of a soft anchor in the inframandibular region and a buttress for the tongue implant. These devices also preferably use materials having long-term biocompatibility.

Although various embodiments disclosed herein relate to use in humans, it is contemplated that the present invention may be used in all mammals, and in all animals having air passages. Moreover, the systems, devices, and methods disclosed herein may incorporate any materials that are biocompatible, as well as any solutions or components that minimize rejection, enhance tissue ingrowth, enhance the formation of mucosal layers, and improve acceptance of the device by a body after the device has been implanted.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A system for treating obstructive sleep apnea comprising:
   a substantially flat, planar first implant adapted for implantation in an inframandibular region and having at least one aperture therethrough extending between a top surface and a bottom surface of the implant, the first implant further comprising a substantially flat, planar cover portion, and a substantially flat, planar base portion coupled to the cover portion around a peripheral edge so as to form a pouch therebetween, and a substantially flat, planar anchor element positioned within said pouch between said cover portion and base portion, wherein the aperture therethrough extends through the cover portion, base portion and anchor element; and
   a ribbon element having first and second ends and a substantially uniform, non-circular cross-section along an entire length thereof, wherein the ribbon-like element is adapted for implantation in a tongue with the first and second ends extending through the at least one aperture in the first implant for coupling said ribbon-like element with said first implant.

2. The system according to in claim 1, wherein said anchor element has a stiffness greater than said cover and base portions.

3. The system according to claim 2, wherein the anchor element is comprised of a biocompatible, non-resorbable material selected from the group consisting of silicon, polyurethane, polypropylene, polyethylene, polyurethane, stainless steel, nitinol, tantalum and titanium.

4. The system according to in claim 1, wherein said cover and base portions are comprised of a biocompatible mesh or a biocompatible fabric.

5. The system according to claim 4, wherein the mesh or fabric is a resorbable mesh or fabric.

6. The system according to claim 1, wherein the anchor element is comprised of a mesh.

7. The system according to claim 1, wherein the ribbon-like element is comprised of polytetrafluoroehtylene.

\* \* \* \* \*